United States Patent
Endo et al.

(10) Patent No.: US 11,055,799 B2
(45) Date of Patent: Jul. 6, 2021

(54) INFORMATION PROCESSING METHOD AND RECORDING MEDIUM

(71) Applicant: Panasonic Intellectual Property Management Co., Ltd., Osaka (JP)

(72) Inventors: Mitsuru Endo, Tokyo (JP); Katsuyoshi Yamagami, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1053 days.

(21) Appl. No.: 15/627,350

(22) Filed: Jun. 19, 2017

(65) Prior Publication Data

US 2018/0005333 A1    Jan. 4, 2018

(30) Foreign Application Priority Data

Jul. 1, 2016  (JP) .............................. JP2016-131739
Jan. 26, 2017  (JP) .............................. JP2017-012528

(51) Int. Cl.
*G16H 50/20* (2018.01)
*G06Q 50/22* (2018.01)
(Continued)

(52) U.S. Cl.
CPC ............. *G06Q 50/22* (2013.01); *G16H 10/20* (2018.01); *G16H 50/20* (2018.01); *G06F 3/0488* (2013.01);
(Continued)

(58) Field of Classification Search
CPC ......... G16H 10/20; G16H 10/60; G06Q 50/24
See application file for complete search history.

(56) References Cited

U.S. PATENT DOCUMENTS

2014/0122109 A1   5/2014  Ghanbari et al.
2016/0148114 A1*  5/2016  Allen ...................... G06N 5/02
                                                                706/11
(Continued)

FOREIGN PATENT DOCUMENTS

JP    2010-129033       6/2010
JP    2015-225402 A    12/2015
(Continued)

OTHER PUBLICATIONS

The EPC Office Action dated Apr. 29, 2020 for the related European Patent Application No. 17176796.5.
(Continued)

*Primary Examiner* — Reginald R Reyes
(74) *Attorney, Agent, or Firm* — Greenblum & Bernstein, P.L.C.

(57) ABSTRACT

An information processing method in an interactive apparatus that questions a user's symptom through interaction with a user includes: outputting first question information of a first type concerning the user's symptom to a display or a speaker connected to the interactive apparatus, receiving first answer information indicating an answer to the question in the first question information from a keyboard, a touch panel, or a microphone connected to the interactive apparatus, outputting second question information of the first type concerning the user's symptom to the display or the speaker when it is determined that the answer in the first answer information does not include a word in a negative expression, and outputting third question information of a second type concerning the user's symptom to the display or the speaker when it is determined that the answer in the first answer information includes the word in the negative expression.

10 Claims, 13 Drawing Sheets

(51) Int. Cl.
*G16H 10/20* (2018.01)
*G06F 3/0488* (2013.01)
*G06F 3/0489* (2013.01)
*G06Q 50/16* (2012.01)
*H04R 1/02* (2006.01)

(52) U.S. Cl.
CPC ........... *G06F 3/0489* (2013.01); *G06Q 50/16* (2013.01); *H04R 1/021* (2013.01)

(56) References Cited

U.S. PATENT DOCUMENTS

2016/0171177 A1\* 6/2016 Caffarel ................. G06Q 40/08 705/3
2019/0244684 A1\* 8/2019 Hussam ................. G16H 10/20

FOREIGN PATENT DOCUMENTS

JP 2016-001242 A 1/2016
WO 2013/166146 A1 11/2013

OTHER PUBLICATIONS

Jeronimo Pellegrini et al: "On the use of POMDPs to model diagnosis and treatment of diseases",IV Encontro Nacional de Inteligencia Artificial, 2003, XP055427364.

Steve Young et al., "The Hidden Information State model: A practical framework for POMDP-based spoken dialogue anagement", Computer Speech and Language 24 (2010), 150-174, Apr. 2, 2010.

The Extended European Search Report dated Nov. 29, 2017 for the related European Patent Application No. 17176796.5.

Yasuhiro Minami, et al, "POMDP Dialogue Control Based on Predictive Action Probability Obtained from Dialogue Act Trigram Sequence" , IEICE Transactions, Japan, the Institute of Electronics, Information and Communication Engineers, Jan. 1, 2012 (Jan. 1, 2012), vol. J95-A, No. 1, pp. 2-15.

\* cited by examiner

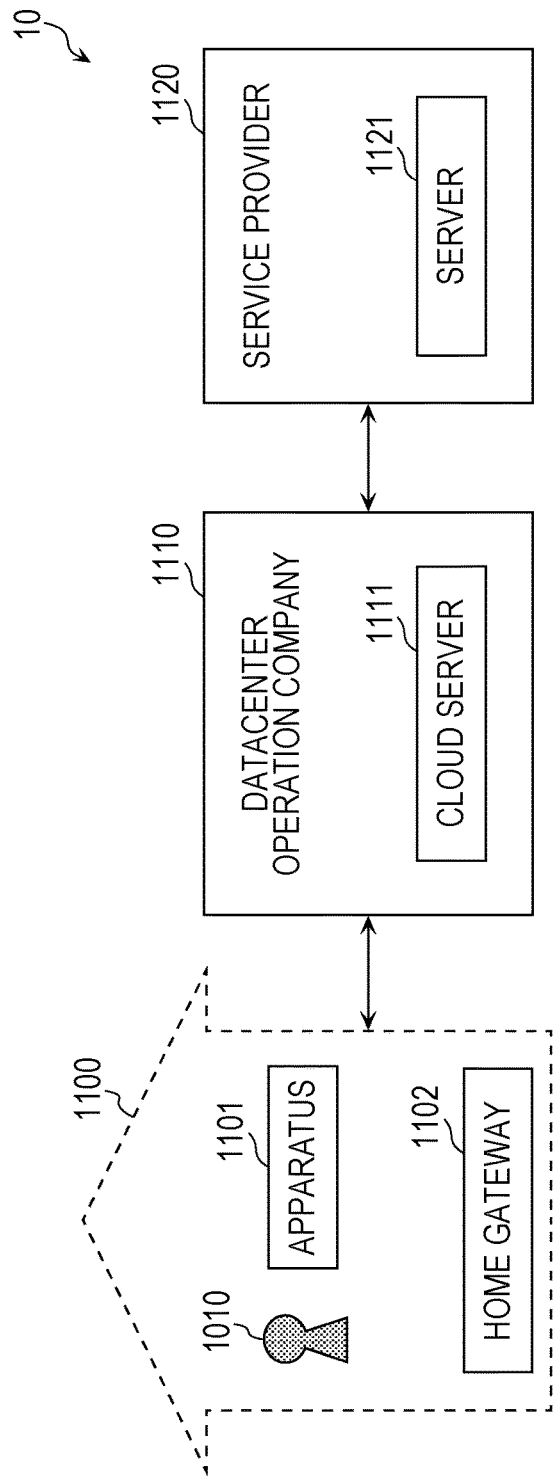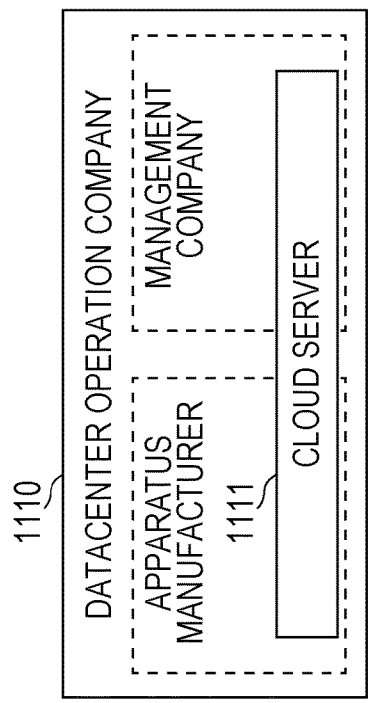

|  |  | SEARCH TARGET NAME | | | |
|---|---|---|---|---|---|
|  |  | DISEASE 1 | DISEASE 2 | DISEASE 3 | DISEASE 4 |
| SEARCH KEYWORD | SYMPTOM A | + | + | − | − |
|  | SYMPTOM B | + | − | + | − |
|  | SYMPTOM C | + | − | − | − |
|  | SYMPTOM D | − | + | − | − |
|  | SYMPTOM E | − | − | + | − |
|  | SYMPTOM F | − | − | − | + |

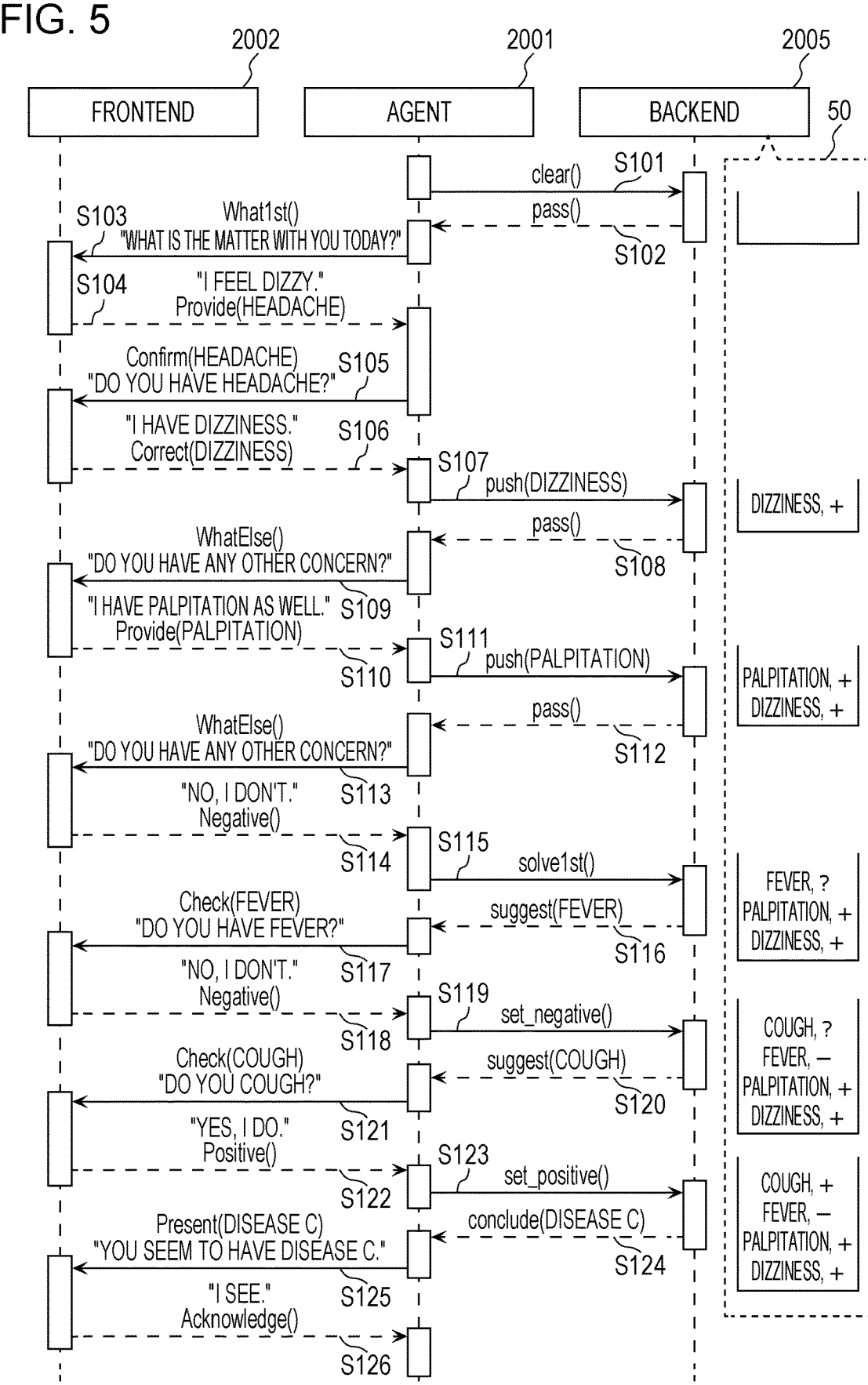

|  | CORRECT ANSWER RATE | AVERAGE NUMBER OF TURNS | AVERAGE REWARD |
| --- | --- | --- | --- |
| NO CONFIRMATION STRATEGY | 75.7% | 10.2 | 98.7 |
| CONFIRMATION STRATEGY (HAND-CRAFTED) | 80.5% | 10.1 | 102.3 |
| CONFIRMATION STRATEGY (REINFORCEMENT LEARNING) | 85.6% | 9.7 | 103.8 |

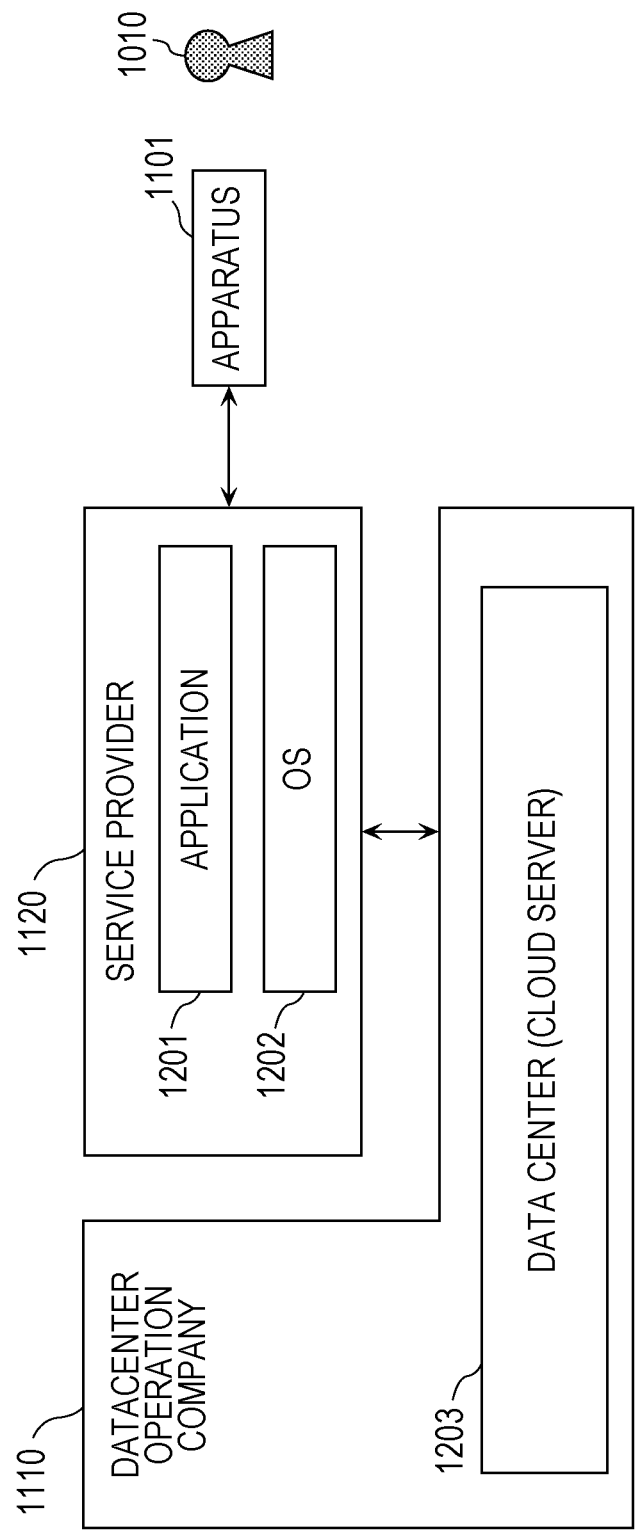

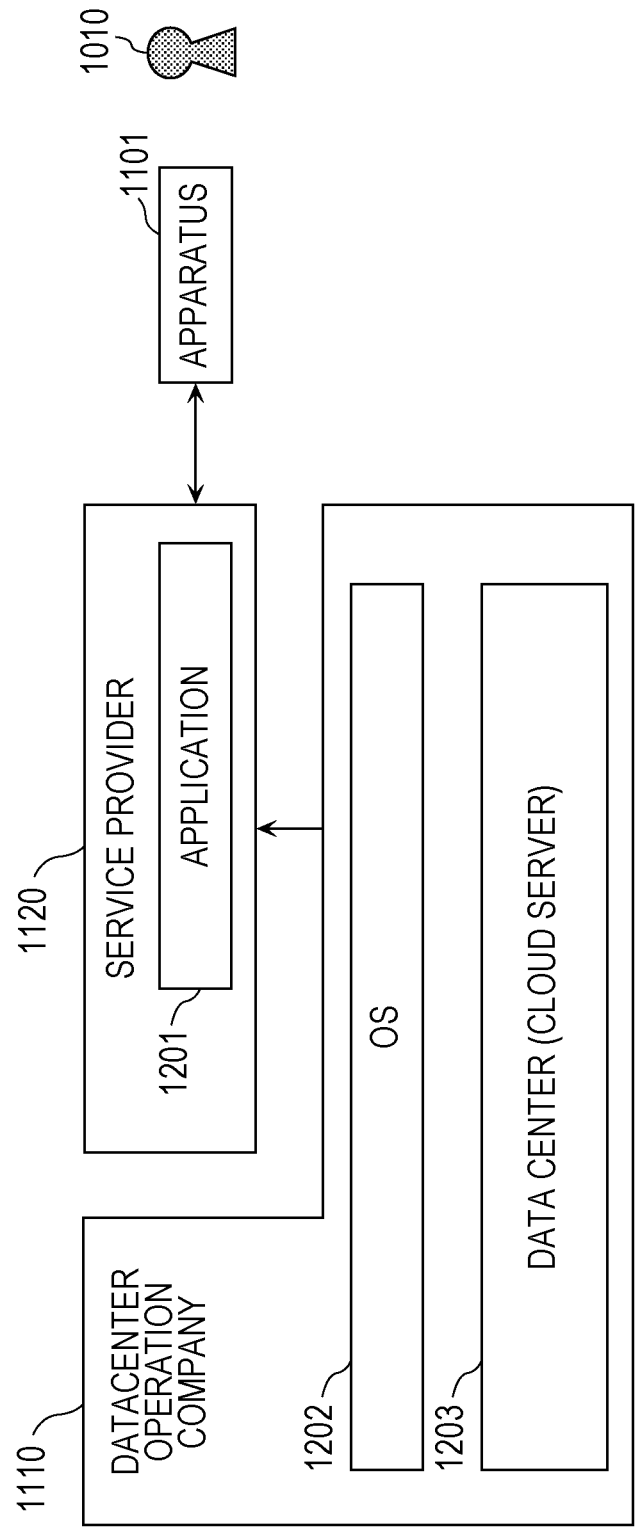

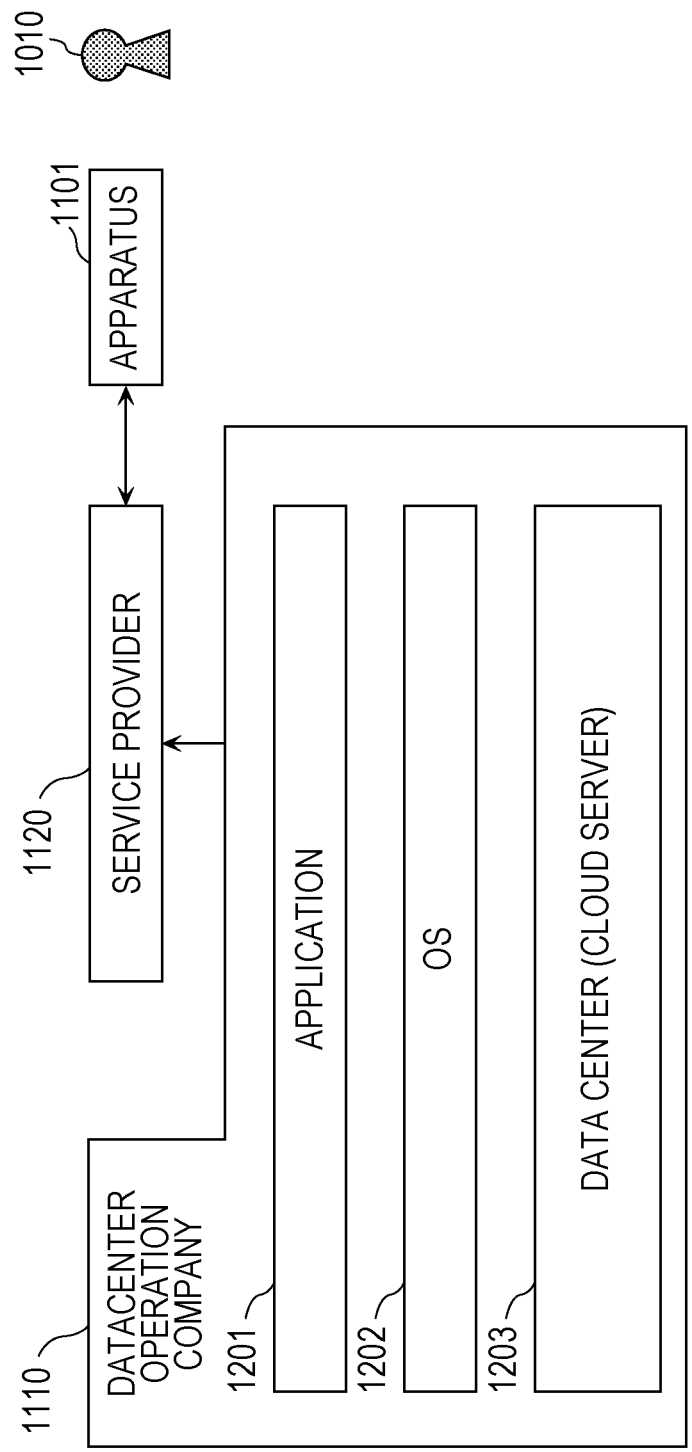

INFORMATION PROCESSING METHOD AND RECORDING MEDIUM

BACKGROUND

1. Technical Field

The present disclosure relates to an interactive system to interact with a user and perform information processing, and relates to an agent apparatus, an interactive method, and a computer program used in the interactive system.

2. Description of the Related Art

There has been known a system that interacts with a user using an apparatus such as a computer to identify necessary information. The system needs to perform appropriate control according to an interaction state with the user.

SUMMARY

In order for an interactive system to carry out a large-scale task for deriving several thousand or more conclusions, it is necessary to efficiently perform control corresponding to an interaction state.

In one general aspect, the techniques disclosed here feature an information processing method in an interactive apparatus that questions a symptom of a user through interaction with the user, the information processing method including: outputting first question information of a first type concerning the symptom of the user to a display connected to the interactive apparatus or a speaker connected to the interactive apparatus, the first question information indicating an open question; receiving first answer information indicating an answer to the question indicated by the first question information from a keyboard connected to the interactive apparatus, a touch panel connected to the interactive apparatus, or a microphone connected to the interactive apparatus; outputting second question information of the first type concerning the symptom of the user to the display or the speaker when it is determined that the answer indicated by the first answer information does not include a word in a negative expression, the second question information indicating an open question; and outputting third question information of a second type concerning the symptom of the user to the display or the speaker when it is determined that the answer indicated by the first answer information includes the word in the negative expression, the third question information indicating a closed question.

These general and specific aspects may be implemented using a system, a method, and a computer program, and any combination of systems, methods, and computer programs.

According to the present disclosure, further improvements are realized.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1A is a conceptual diagram showing an example of a form of a service provided by an interactive system according to an embodiment;

FIG. 1B is a conceptual diagram showing an example of a datacenter operation company according to the embodiment;

FIG. 5 is a sequence chart showing an example of a sequence of interaction in the interactive system according to the embodiment;

FIG. 9 is a conceptual diagram showing a service (a type 2) provided by the interactive system;

FIG. 10 is a conceptual diagram showing a service (a type 3) provided by the interactive system; and FIG. 11 is a conceptual diagram showing a service (a type 4) provided by the interactive system.

Figure 2:
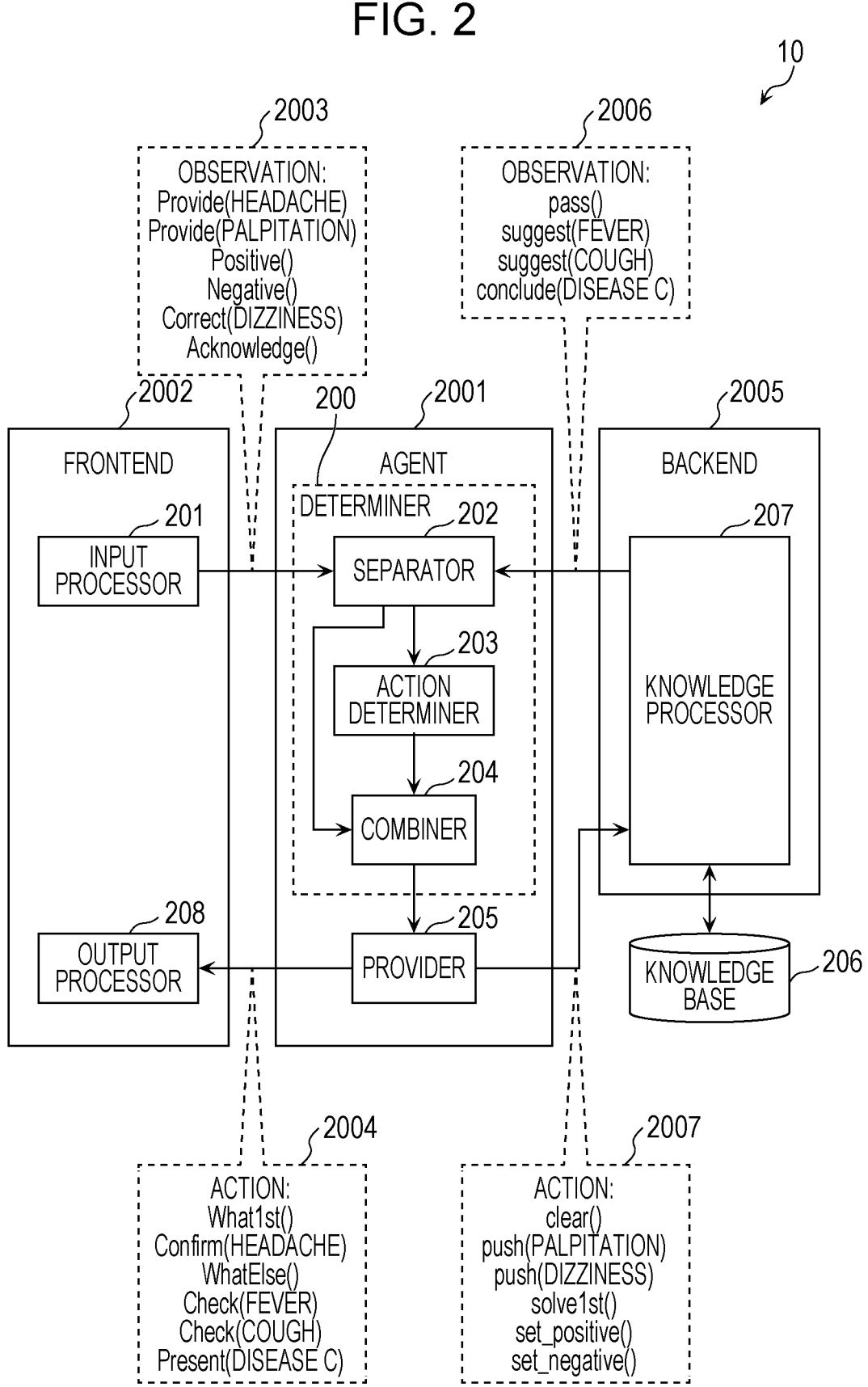
FIG. 2 is a schematic configuration diagram of the interactive system according to the embodiment.

DETAILED DESCRIPTION (Underlying Knowledge Forming Basis of the Present Disclosure)

There are many scenes in which an expert having abundant expert knowledge and a general person having poor expert knowledge exchange information through dialog to carry out a task of specifying information serving as a conclusion satisfied by both the expert and the general person. Examples of such tasks include a medical interview between a doctor and a patient. In the medical interview, a doctor who has expert knowledge but does not have information on a subjective symptom of a patient and the patient who has poor expert knowledge but can provide information on the symptom of the patient by answering questions or voluntarily talking about the symptom have conversations to increase an amount of information serving as clues and thereby to reflect the information on a conclusion (a diagnosis result). An interactive system has been examined which uses a machine such as a computer to carry out a task of identifying information to serve as a conclusion through dialog with a general user such as a medical interview. For example, interaction control by the POMDP model is capable of handling an uncertain input including errors of voice recognition, language understanding, and the like, and therefore can be expected to optimize action selection for performing just sufficient confirmation and other acts for a user.

However, in the example of the medical interview, the number of candidates of diseases that could be a conclusion of the medical interview (diagnosis result) is as many as several thousand or more. That is, to express a process for identifying candidates for a disease as a transition of states based on information obtained from the patient requires several thousand or more states including logical conditional branches and conclusions. When the number of states necessary for the interaction control (interaction states) is as many as several thousand or more, a high computation load is required to optimize action selection among confirmation and other acts for the user. For example, a large computer resource could be necessary for the interaction control. A technique for carrying out a large-scale task through a small-scale interaction control has not been examined.

Therefore, the present inventor has studied on improvement measures explained below.

(1) An information processing method according to an aspect of the present disclosure provides an information processing method in an interactive apparatus that questions a symptom of a user through interaction with the user, the information processing method including: outputting first question information of a first type concerning the symptom of the user to a display connected to the interactive apparatus or a speaker connected to the interactive apparatus, the first question information indicating an open question; receiving first answer information indicating an answer to the question indicated by the first question information from a keyboard connected to the interactive apparatus, a touch panel connected to the interactive apparatus, or a microphone connected to the interactive apparatus; outputting second question information of the first type concerning the symptom of the user to the display or the speaker when it is determined that the answer indicated by the first answer information does not include a word in a negative expression, the second question information indicating an open question; and outputting third question information of a second type concerning the symptom of the user to the display or the speaker when it is determined that the answer indicated by the first answer information includes the word in the negative expression, the third question information indicating a closed question.

(2) In the described-above aspect, the information processing method may include: receiving second answer information from the keyboard connected to the interactive apparatus, the touch panel connected to the interactive apparatus, or the microphone connected to the interactive apparatus, the second answer information indicating the presence or absence of the symptom indicated by the third question information of the second type; determining the presence or absence of the symptom indicated by the third question information based on the second answer information; when it is determined that the symptom indicated by the third question information is present, classifying the symptom indicated by the third question information as a designated keyword; when it is determined that the symptom indicated by the third question information is absent, classifying the symptom indicated by the third question information as an excluded keyword; and outputting information to the touch panel connected to the interactive apparatus or the microphone connected to the interactive apparatus, the information indicating a symptom of the user identified based on a combination of the designated keyword and the excluded keyword.

(3) In the described-above aspect, the open question may be a question other than a question to be answered by yes or no, and the closed question is a question to be answered by yes or no.

(4) An information processing method according to another aspect of the present disclosure provides an information processing method in an interactive apparatus that interacts with a user to narrow down items to an item that the user desires to find, the information processing method including: outputting first question information of a first type concerning the item that the user desires to find to a display connected to the interactive apparatus or a speaker connected to the interactive apparatus, the first question information indicating an open question; receiving first answer information indicating an answer to the question indicated by the first question information from a keyboard connected to the interactive apparatus, a touch panel connected to the interactive apparatus, or a microphone connected to the interactive apparatus; outputting second question information of the first type concerning the item that the user desires to find to the display or the speaker when it is determined that the answer indicated by the first answer information does not include a word in a negative expression, the second question information indicating an open question; and outputting third question information of a second type concerning the item that the user desires to find to the display or the speaker when it is determined that the answer indicated by the first answer information includes the word in the negative expression, the third question information indicating a closed question.

(5) In the described-above another aspect, the item that the user desires to find may be any of a disease name, a recipe of a dish, a travel plan, a real estate property, and a video content.

Note that these comprehensive and concrete forms may be realized as a system, a method, an integrated circuit, a computer program, or a computer-readable recording medium such as a CD-ROM or may be realized as any combination of the system, the method, the integrated circuit, the computer program, and the recording medium.

Embodiments of the present disclosure are explained in detail below with reference to the drawings. Note that all of the embodiments explained below indicate comprehensive or concrete examples of the present disclosure. Numerical values, shapes, components, dispositions of the components, steps, order of the steps, and the like explained in the following embodiments are examples and do not limit the present disclosure. Among the components in the following embodiments, components not described in independent claims are components that can be optionally added. Figures are schematic figures and are not always strictly illustrated.

(Overview of a Provided Service)

First, a form of a service provided by an interactive system in an embodiment is explained.

FIG. 1A is a diagram showing an example of a form of a service provided by an interactive system 10 in this embodiment. The interactive system 10 includes a group 1100, a datacenter operation company 1110, and a service provider 1120.

The group 1100 is a facility (e.g., a building or a house) of, for example, a company, an organization, or a home. The size of the group 1100 may be any size. The group 1100 includes an apparatus 1101 and a home gateway 1102. The apparatus 1101 includes a user interface for exchanging information with a user according to some method. The apparatus 1101 is, for example, an apparatus connectable to the Internet (e.g., a smartphone, a personal computer (PC), or a television). Note that the apparatus 1101 may be an apparatus not connectable to the Internet by itself (e.g., a washing machine or a refrigerator) or may be an apparatus connectable to the Internet via the home gateway 1102. Note that the home gateway 1102 is sometimes unnecessary. A user 1010 uses the apparatus 1101. The apparatus 1101 may be a portable apparatus connectable to the Internet by radio (e.g., a smartphone or a notebook PC). In this case, the user 1010 and the apparatus 1101 do not always have to be present within the group 1100. Note that the apparatus 1101 is not limited to one apparatus and may be configured by a plurality of apparatuses.

The datacenter operation company 1110 includes a cloud server 1111. The cloud server 1111 is a computer cooperating with various apparatuses via the Internet and is, for example, a virtual server. The cloud server 1111 manages, for example, big data that is hard to be treated by a normal database management tool or the like. The datacenter operation company 1110 performs management of data, management of the cloud server 1111, and the like. Note that the datacenter operation company 1110 is not limited to a management company that performs only the management of data and the management of the cloud server 1111. The datacenter operation company 1110 may be a company that performs other businesses as well, for example, an apparatus manufacturer that develops or manufactures the apparatus 1101. The datacenter operation company 1110 is not limited to one company. For example, as shown in FIG. 1B, when an apparatus manufacturer and a management company cooperate or share responsibilities to perform the management of data and the management of the cloud server 1111, both of the apparatus manufacturer and the management company could correspond to the datacenter operation company 1110.

The service provider 1120 includes a server 1121. The server 1121 is realized by, for example, one or a plurality of computers. The size of the server 1121 may be any size. The server 1121 may include a storage such as a large-capacity hard disk as a storage medium or may include, for example, only a memory in a PC. Note that the server 1121 does not always have to include the storage medium.

A flow of information in the interactive system 10 having the form explained above is explained.

First, the apparatus 1101 of the group 1100 transmits input information acquired via the user interface to the cloud server 1111 of the datacenter operation company 1110 directly or via the home gateway 1102. The user interface used for input of the input information by the user 1010 in the apparatus 1101 is, for example, a keyboard, a touch panel, or a voice input device (a microphone) in which an existing voice recognition technique is used. The cloud server 1111 acquires the input information transmitted from the apparatus 1101.

Subsequently, the cloud server 1111 of the datacenter operation company 1110 transmits information based on the input information, which is transmitted from the apparatus 1101, to the server 1121 of the service provider 1120. The information based on the input information may be information including information same as at least a part of the input information or may be information not including the same information and obtained as a result of applying processing such as an arithmetic operation to the input information. A unit of the transmission of the information based on the input information may be any unit. The server 1121 acquires information transmitted from the cloud server 1111.

The server 1121 of the service provider 1120 identifies information for provision to the user according to the information transmitted from the cloud server 1111 and transmits the information for provision to the cloud server 1111 in order to provide the information for provision to the user 1010. The cloud server 1111 transfers the information for provision, which is transmitted from the server 1121, to the apparatus 1101 or transmits information obtained as a result of applying processing such as an arithmetic processing to the information for provision to the apparatus 1101. Consequently, the information is provided from the user interface of the apparatus 1101 to the user 1010. The user interface used for the provision of the information to the user 1010 in the apparatus 1101 is, for example, a display or a voice output device (a speaker) in which an existing speech synthesis technique is used.

Note that the server 1121 may perform communication with the apparatus 1101 not via the cloud server 1111 to perform the acquisition of the input information from the user 1010 and the provision of the information for provision. The interactive system 10 may adopt a form different from the example explained above. For example, in the interactive system 10, the datacenter operation company 1110 and the service provider 1120 may be omitted. The apparatus 1101 may identify the information for provision based on the input information acquired from the user and provide the information for provision to the user.

First Embodiment (Configuration)

A configuration for performing an interactive method for exchanging information with the user in the interactive system 10 employing the POMDP model is explained as an example.

In general, the POMDP model is defined by model elements, that is, a set S of states, a set A of actions, a set Z of observations, a state transition matrix T, an observation matrix O, a reward matrix R, and an initial state BO of a belief state. In the conventional interactive system employing the POMDP model in which an agent observes a present state and determines an action that the agent should take in a certain environment, a user is associated with the environment, a system (a computer system) is associated with the agent, a dialogue act of the user is regarded as observation, and a dialogue act of the system is regarded as an action. On the other hand, in the interactive system 10, modeling in a structure including one agent and two environments is performed.

FIG. 2 is a schematic configuration diagram of the interactive system 10.

As shown in FIG. 2, the interactive system 10 includes an agent 2001, a frontend 2002 functioning as a first environment, a backend 2005 functioning as a second environment, and a knowledge base 206.

The agent 2001 is an apparatus functioning as an interactive agent (an agent apparatus). The agent 2001 can be implemented in a computer including, for example, a processor (a microprocessor) and a memory. Specifically, for example, the processor executes a computer program stored in the memory, whereby a function of the agent 2001 can be realized. The agent 2001 mediates exchange of a dialogue act between the frontend 2002 and the backend 2005. That is, the agent 2001 performs the exchange of the dialogue act with each of the frontend 2002 and the backend 2005. The dialogue act is information of a predetermined form (a predetermined interactive act form) configured by a dialogue act type and incidental information.

The frontend 2002 is an apparatus that performs user interface processing. The frontend 2002 exchanges information expressed in a natural language with the user. The frontend 2002 can be implemented in, for example, computer same as or different from the agent 2001. A function of the frontend 2002 can be realized by, for example, a user interface of the computer and a processor that executes a computer program stored in a memory of the computer.

The backend 2005 is an apparatus that performs information processing such as search processing. The backend 2005 performs knowledge processing including provision of information based on an inquiry (search processing) to the knowledge base 206. The backend 2005 can be implemented in, for example, a computer same as or different from the agent 2001. A function of the backend 2005 can be realized by, for example, a communication interface of the computer and a processor that executes a computer program stored in a memory of the computer.

When the agent 2001 and each of the frontend 2002 and the backend 2005 are realized by a plurality of apparatuses apart from each other, the agent 2001 and each of the frontend 2002 and the backend 2005 communicate directly or via another apparatus.

The knowledge base 206 is an apparatus that retains information and is, for example, a database management apparatus that structures and manages data representing information. The knowledge base 206 can be implemented in, for example, a computer same as or different from the backend 2005. The knowledge base 206 can be realized by, for example, a storage medium such as a memory or a hard disk in the computer. In the interactive system 10 for carrying out a medical interview task, the knowledge base 206 retains information useful for carrying out the medical interview task (e.g., information related to symptoms and diseases). The knowledge base 206 may be configured by a plurality of apparatuses.

In FIG. 2, a dialogue act in the interactive system 10 for carrying out the medical interview task is illustrated. An observation 2003 is an example of a dialogue act acquired by the agent 2001 from the frontend 2002. An observation 2006 is an example of a dialogue act acquired by the agent 2001 from the backend 2005. An action 2004 is an example of a dialogue act provided to the frontend 2002 by the agent 2001. An action 2007 is an example of a dialogue act provided to the backend 2005 by the agent 2001. All of the observation 2003, the observation 2006, the action 2004, and the action 2007 are examples of information (a dialogue act) of a predetermined interactive act form. In a dialogue act of character string information in this example, portions before parentheses (e.g., "Provide" and "Confirm") are a dialogue act type and portions in the parentheses (e.g., "dizziness" and "headache") are incidental information. The dialogue act type represents any one of, for example, a plurality of values (interactive act type values) such as "Provide", "Confirm", "Check", and "push" decided in advance. The dialogue act type values are represented by, for example, character strings. In this example, the dialogue act type values are represented by English words. However, this is only an example. The dialogue act type values may be represented based on any language or any rule. The incidental information is, for example, character string information indicating a keyword.

In the interactive system 10, a task is carried out according to a series of a dialogue act exchanged between the agent 2001 and a set of the frontend 2002 and the backend 2005. In an example of the medical interview task, a disease is identified by the backend 2005 based on information collected to the agent 2001 from the user in an interactive manner via the frontend 2002.

More detailed configurations of the agent 2001, the frontend 2002, and the backend 2005 are explained below.

As shown in FIG. 2, the frontend 2002 includes an input processor 201 and an output processor 208 related to user interface processing. The agent 2001 includes a determiner 200 and a provider 205. The backend 2005 includes a knowledge processor 207.

The determiner 200 assumes a function for determining a dialogue act for provision to one of the frontend 2002 and the backend 2005 according to a dialogue act acquired from one of the frontend 2002 and the backend 2005. In order to realize the function, the determiner 200 includes a separator 202, an action determiner 203, and a combiner 204. Note that the determiner 200 can be configured to determine a dialogue act type in the dialogue act for provision based on a series of a dialogue act type determined in the past.

The input processor 201 converts, with an existing natural language processing technique (e.g., a language understanding technique), a natural language expression (a character string), which is an input from the user by, for example, a user interface such as a keyboard, a touch panel, or a voice input device (a microphone), adds reliability to the dialogue act, and outputs the dialogue act. Consequently, the dialogue act and the reliability are acquired by the separator 202. When the input from the user is voice, the input processor 201 may perform preprocessing for converting the input voice into a character string with a voice recognition technique.

The separator 202 separates the dialogue act acquired from the input processor 201 of the frontend 2002 or the knowledge processor 207 of the backend 2005 into a dialogue act type and incidental information. For example, a dialogue act "Provide (headache)" is separated into a dialogue act type "Provide" and incidental information "headache". The separator 202 inputs the separated interactive act type to the action determiner 203. That is, the separator 202 sequentially acquires interactive acts from the set of the frontend 2002 and the backend 2005 and separates incidental information from the acquired interactive acts to sequentially input series of interactive act types to the action determiner 203 as observations. The separator 202 inputs the separated incidental information to the combiner 204.

The action determiner 203 determines, with an existing action determination technique employing the POMDP model, a dialogue act type serving as an action based on series of interactive act types sequentially input as observations and putouts the dialogue act type. For example, a dialogue act type "push" is determined and output by the action determiner 203. An existing technique can be used for learning of a policy referred to in the POMDP model. Note that, in a case in which a probability distribution (also referred to as belief state) of a state treated in the POMDP takes only values of 0 or 1, a model can be regarded as a Markov decision process (MDP) model. That is, determination of an action by the action determiner 203 includes determination of an action by the MDP model as well. In these models (the POMDP model and the MDP model), optimization of a policy referred to for selective action determination can be performed by reinforcement learning. Note that the action determiner 203 determines an action referring to the belief state and the policy based on the observation. The action determiner 203 retains belief state information serving as information indicating the belief state and can update the belief state information according to the observation and the determined action. The action determiner 203 may retain a history of interactive act types serving as determined actions. The action determiner 203 may perform the determination of the dialogue act type serving as the action based on series of interactive act types serving as actions determined in the past.

The combiner 204 combines the dialogue act type determined and output by the action determiner 203 based on the dialogue act type separated by the separator 202 and the incidental information separated by the separator 202 to generate and output a dialogue act for provision. For example, a dialogue act "push (headache)" is output by the combiner 204.

The provider 205 assumes a function of providing the dialogue act for provision determined by the determiner 200 to one of the frontend 2002 and the backend 2005. The provider 205 can switch an environment serving as an output destination of the dialogue act output from the combiner 204 to one of the frontend 2002 and the backend 2005. Specifically, the provider 205 determines based on a reference decided in advance in order to distinguish the output destination of the dialogue act whether the output destination of the dialogue act for provision should be set as the output processor 208 or the knowledge processor 207. The reference decided in advance is, for example, a reference for distinguishing the output destination according to whether a leading character of the dialogue act is an upper case letter or a lower case letter. For example, if a leading character of the dialogue act for provision (i.e., a leading character of the dialogue act type) is an upper case letter as indicated by the action 2004, the provider 205 outputs the dialogue act to the output processor 208. For example, if the leading character of the dialogue act for provision (i.e., the leading character of the dialogue act type) is a lower case letter as indicated by the action 2007, the provider 205 outputs the dialogue act to the knowledge processor 207.

The output processor 208 converts, with an answer sentence generation technique (e.g., an existing sentence generation technique), meaning expression indicated by the dialogue act output from the provider 205 into an answer sentence and provides the answer sentence to the user as a character string. The provision of the character string to the user is performed by, for example, a user interface such as a display or a voice output device (a speaker). The output processor 208 may perform post-processing for converting the character string that should be provided to the user into voice with a voice synthesis technique.

The knowledge processor 207 performs, referring to the knowledge base 206, information processing corresponding to the dialogue act output from the provider 205 and provides a dialogue act indicating a result of the information processing to the separator 202. The information processing in the knowledge processor 207 is, for example, search processing for searching and extracting information from the knowledge base 206. The knowledge processor 207 performs, for example, search processing for setting, as a set of search keywords (keywords for search), a list of keywords serving as character strings represented by incidental information in interactive acts acquired to that point from the agent 2001 and performing an AND search of contents of the knowledge base. The knowledge processor 207 generates a dialogue act based on a result of the search processing and provides the generated interactive act to the separator 202 of the agent 2001. For example, the knowledge processor 207 determines whether the result of the search processing is sufficiently narrowed down. If a predetermined condition (e.g., a condition such as an upper limit of the number of kinds of searched information) decided in advance is satisfied to indicate that the result is sufficiently narrowed down and the knowledge processor 207 determines that the result is sufficiently narrowed down, the knowledge processor 207 generates a dialogue act indicating the search result and outputs the dialogue act (provides the dialogue act to the separator 202). On the other hand, if the knowledge processor 207 determines that the result is not sufficiently narrowed down, the knowledge processor 207 estimates a keyword (a search keyword) effective for narrowing down the result of the search processing, generates a dialogue act indicating the keyword, and outputs the dialogue act (provides the dialogue act to the separator 202). An example of the dialogue act indicating the keyword effective for narrowing down the result of the search processing is, for example, "suggest (fever)" including "fever" as incidental information.

Since the configuration explained above is included, the determiner 200 of the agent 2001 can extract interactive act types in sequentially acquired interactive acts and determine, based on series of interactive act types in the past, a dialogue act type in a dialogue act for provision that should be output as an action. That is, the agent 2001 is capable of performing, based on the series of the dialogue act types in the past, determination of a dialogue act type that should be output without performing determination based on incidental information in the dialogue acts.

By determining the dialogue act type based on a type of the dialogue act type (each of interactive act type values) rather than a type of the dialogue act (each of values of the entire interactive act) in this way, the number of interaction states can be reduced. The reduction of the number of interaction states is advantageous for optimization of action selection by reinforcement learning. As a result of the optimization, the agent 2001 can appropriately select, from the frontend 2002, which is one of environments, according to a situation, the action 2004 related to a type and the like of a question for acquiring (collecting) information serving as the observation 2003. As a result of the information processing, the agent 2001 can appropriately select the action 2007 for obtaining the observation 2006 from the backend 2005, which is another one of the environments. Through these selections (e.g., selection of interactive action types having different types of questions), the agent 2001 can perform interactive control processing such as control of a subject person of interaction and control of confirmation of uncertain information.

Note that, concerning the incidental information separated from the dialogue act type in the acquired interactive act, the agent 2001 only has to retain acquired latest one kind of incidental information.

In the backend 2005, if series of acquired incidental information are stacked and managed in a stack, which is one region of the memory or the like, after an interaction start, it is possible to carry out an advanced task in which a plurality of kinds of incidental information are used. According to the information processing in the backend 2005, for example, incidental information representing symptoms such as "headache" and "dizziness" is collected. Diseases such as a "disease A", a "disease B", and a "disease C" can be identified as desired information. The backend 2005 only has to treat the dialogue act type of the acquire interactive act as, for example, a type of a command and perform processing according to only the present interactive act type and does not need to manage a history of interactive act types.

(Operation)

The operation of the interactive system 10 including the configuration explained above is explained below.

Figure 3:
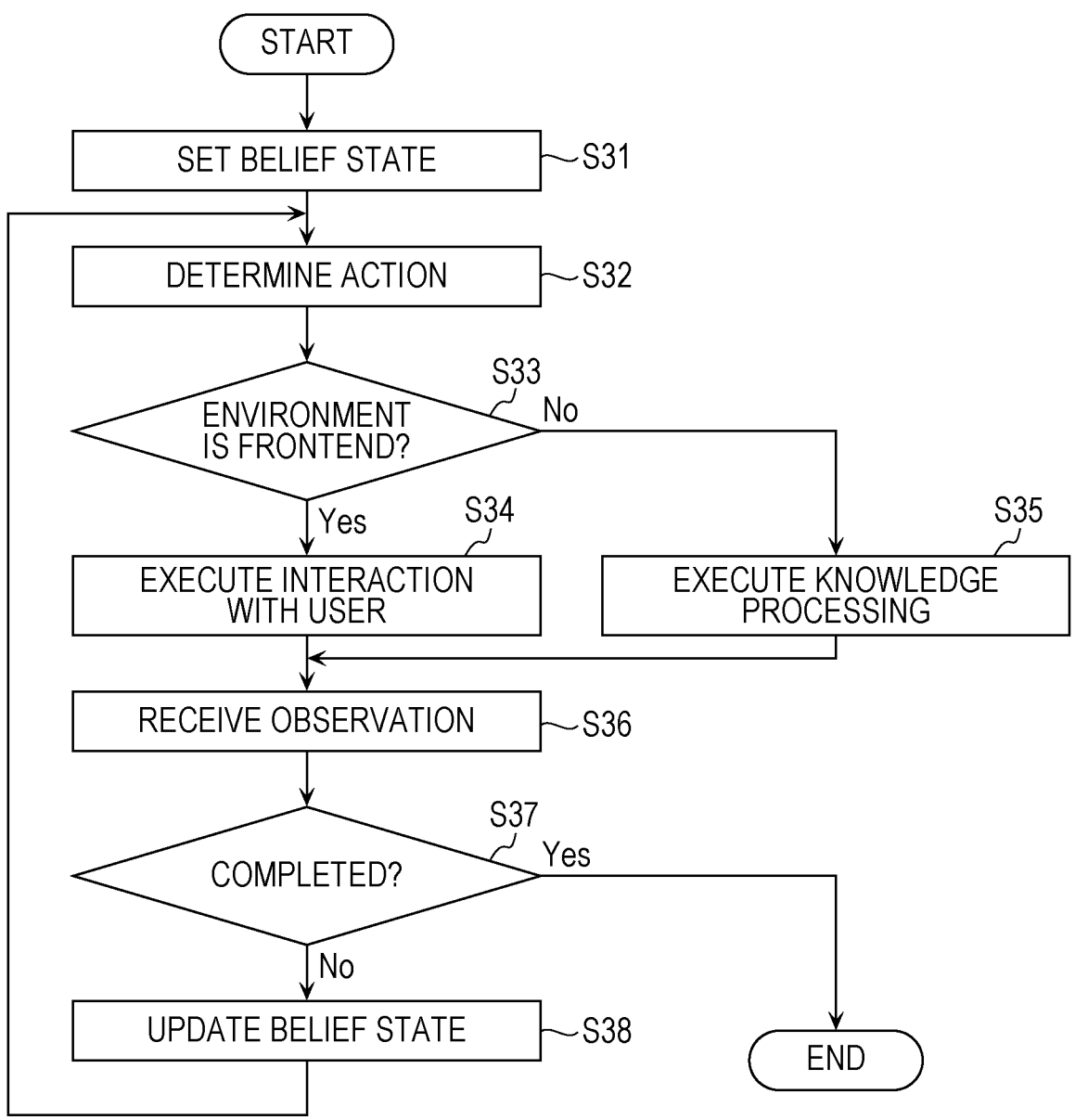
FIG. 3 is a flowchart showing an example of interactive processing in the interactive system according to the embodiment.

FIG. 3 is a flowchart showing an example of interactive processing in the interactive system 10. The operation of the agent 2001 related to interaction is focused and explained below with reference to FIG. 3.

In a start of interaction, first, the agent 2001 sets a belief state (step S31). The belief state is a set of probability values (a probability distribution), a sum of which is 1, with respect to an interaction state defined by a combination of a progress status of interaction and an intention of the user. For example, assuming that the user is in one interaction state at the interaction start time, a probability value of the one state is 1, whereas a probability value of the other state is 0. The belief state is set by the determiner 200 of the agent 2001 retaining, in a storage medium such as a memory, belief state information indicating a belief state serving as an initial state.

The determiner 200 of the agent 2001 determines an action based on the belief state indicated by the belief state information (step S32). Specifically, the action determiner 203 of the determiner 200 refers to a policy, which is a set of references for determining what kind of action should be taken in what kind of belief state, and determines a dialogue act type serving as an action based on the belief state. The determiner 200 communicates a dialogue act for provision including the dialogue act type determined by the action determiner 203 to the provider 205.

Subsequently, the agent 2001 determines whether an environment to which the action determined in step S32 is directed is the frontend 2002 or the backend 2005 (step S33). Specifically, the provider 205 determines an output destination according to the dialogue act for provision based on a reference decided in advance. The provider 205 provides, according to a result of the determination, the dialogue act for provision to either one of the output processor 208 of the frontend 2002 and the knowledge processor 207 of the backend 2005.

If the dialogue act is provided to the frontend 2002, which is one of the environments, from the agent 2001 as a result of the determination in step S33, the frontend 2002 executes interaction with the user (step S34). That is, the output processor 208 of the frontend 2002 converts an action (a dialogue action) of a predetermined interactive act form acquired from the provider 205 into a natural language and presents the natural language to the user. The input processor 201 of the frontend 2002 acquires an answer (a reply) from the user in a form of a natural language, converts the form of the natural language into a form of a dialogue act, and provides the answer to the agent 2001.

On the other hand, if the dialogue act is provided to the backend 2005, which is the other one of the environments, from the agent 2001 as a result of the determination in step S33, the backend 2005 executes knowledge processing (step S35). That is, the knowledge processor 207 of the backend 2005 performs search processing of the knowledge base 206 based on the action (the dialogue act) of the predetermined interactive act form acquired from the provider 205, converts information based on a result of the search processing into a form of a dialogue act, and provides the information to the agent 2001. If the dialogue act can be directly used as a command for search (e.g., a command of a machine language) of the knowledge base 206, the knowledge processor 207 executes the command, which is the dialogue act. If the dialogue act cannot be directly used as the command, the knowledge processor 207 converts the dialogue act into the command of the machine language and executes the command. The knowledge processor 207 converts information based on a return value or the like from the knowledge base 206 serving as the result of the search processing into a form of the dialogue act and provides the information to the agent 2001.

Following step S34 or step S35, the agent 2001 receives (acquires) an observation (the dialogue act) of the predetermined interactive act form from the frontend 2002 and the backend 2005 (step S36).

Subsequently, the agent 2001 determines based on the acquired interactive act whether the interactive processing should be ended (step S37). For example, if the agent 2001 acquires, as the observation, a dialogue act "Acknowledge ( )" from the frontend 2002, the agent 2001 determines that the interactive processing should be ended and ends the interactive processing.

If the agent 2001 does not determine in step S37 that the interactive processing should be ended, the agent 2001 updates the belief state based on the present belief state, the determined action (the action of the form of the dialogue act type), and the observation obtained from the environment (the observation of the form of the dialogue act type) (step S38). That is, the determiner 200 updates the belief state information indicating the belief state according to a series of the dialogue act type in the acquired interactive act and a series of the determined interactive act type.

Following step S38, the agent 2001 returns to step S32 and determines an action according to the dialogue act acquired in step S36.

In this way, the interactive processing includes interactive control processing including the next determination step and the next provision step by the agent 2001. In the interactive processing, every time the agent 2001 acquires the dialogue act from either one of the frontend 2002 and the backend 2005 in repeated step S36, the agent 2001 performs the determination step (step S32) for determining a dialogue act for provision according to the acquired interactive act. Then, the agent 2001 performs a provision step (steps S33 to S35) for providing the dialogue act for provision determined in the determination step to either one of the frontend 2002 and the backend 2005. In the determination step, the agent 2001 determines a dialogue act type in the dialogue act for provision not based on series of incidental information but based on series of interactive act types in interactive acts sequentially acquired from the set of the frontend 2002 and the backend 2005. The agent 2001 can update the belief state based on the series of the dialogue act types and determines a dialogue act type serving as an action based on the belief state.

In this way, the belief state in the agent 2001 is sequentially updated according to the dialogue act type of the action and the dialogue act type of the observation into a belief state reflecting all of series of interactive act types after the start of the interactive processing. Therefore, if the agent 2001 determines an action based on the belief state, the agent 2001 can perform an action matching a progress state of interaction and matching an intention of the user.

An example of knowledge processing, which is a type of information processing in the backend 2005, is explained with reference to FIGS. 4A and 4B.

Figures 4A, 4B:
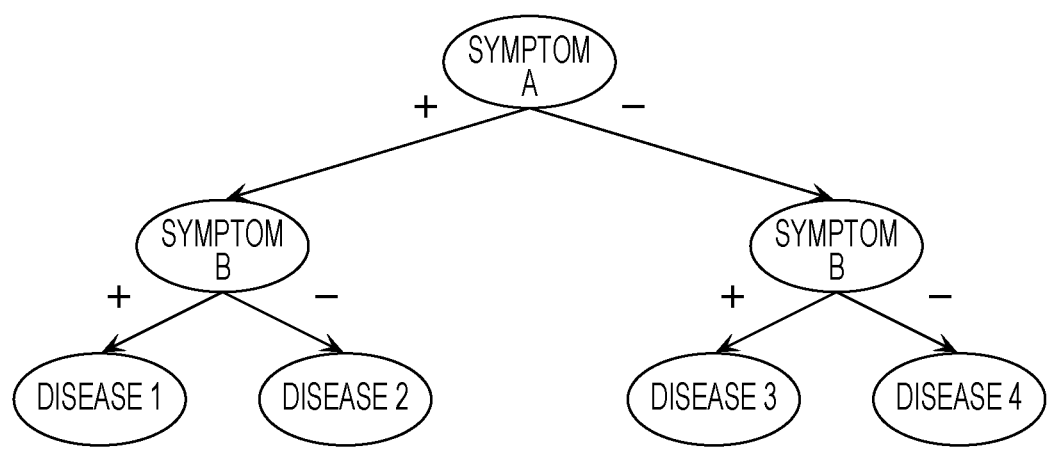
FIG. 4A is a diagram showing an example of a knowledge base according to the embodiment.
FIG. 4B is a conceptual diagram showing an example of knowledge processing according to the embodiment.

FIG. 4A is a diagram showing an example of the knowledge base 206 referred to by the backend 2005.

The knowledge base 206 is a database, which is a search target in the knowledge processing by the knowledge processor 207 of the backend 2005. For example, knowledge for searching for diseases using symptoms as search keywords is structured and managed in the knowledge base 206. A table of FIG. 4A shows an example of an image of knowledge contents of the knowledge base 206. In the table of FIG. 4A, in a cell at a crossing point of a row of a certain symptom and a column of a certain disease, "+" is described if the symptom is easily developed in the case of the disease and "−" is described if the symptom is less easily developed. The search words may be distinguished as, for example, designated keywords for designating development of the symptoms and excluded keywords for designating non-development of the symptoms to perform the search. It is possible to narrow down relevant diseases from a set of diseases by performing an AND search in a combination of one or more of the designated keywords for designating the symptoms and the excluded keywords. In the example shown in FIG. 4A, a symptom A is set as a designated keyword (+) and a symptom D is set as an excluded keyword (−) to perform the AND search. Then, the relevant disease is only a disease 1. FIG. 4A is only an example for convenience of explanation. In the knowledge base 206, there can be large numbers of (e.g., several ten or several thousand or more) search keywords (e.g., symptoms) and search target names (e.g., diseases).

FIG. 4B is a conceptual diagram in which an example of the knowledge processing by the knowledge processor 207 of the backend 2005 is represented by a question tree.

The example shown in FIG. 4B is an example of a question tree related to performance of a medical interview task of identifying a disease through questions related to symptoms using the knowledge base 206 illustrated in the table of FIG. 4A. For convenience of explanation, a relatively simple question tree is shown. A root node of the question tree shown in FIG. 4B represents a first question. A question concerning whether a symptom A is developed is represented as "symptom A". Leaf nodes indicate diseases identified by questions. Intermediate nodes located between the root node and the leaf nodes represent second and subsequent questions. Arrows (edges) among the nodes correspond to whether an answer to a question is "+" (an answer indicating that a symptom of the question is developed) or "−" (an answer indicating that the symptom of the question is not developed). The entire question tree is a binary tree. In the root node, sets of all diseases are associated. Sets of relevant diseases are sequentially divided by questions to narrow down the diseases. When there are no more question for dividing the sets of the diseases, a set of diseases (one or a plurality of diseases) remaining at that point is a conclusion (a result of the search processing). In the question tree, efficiency of narrow-down of candidates is different depending on the order of questions. In order to reduce the number of times of questions in the worst case, it is desirable to select questions with which a ratio of "+" and "−" of the remaining sets of the diseases is as close as possible to 1:1.

As the operation of the knowledge processor 207 of the backend 2005, the knowledge processor 207 acquires a dialogue act indicating a command from the agent 2001, performs knowledge processing (search processing, etc.) based on the command, and returns (provides) a dialogue act indicating a return value to the command to the agent 2001. More specifically, the knowledge processor 207 stacks, in the stack, as search keywords, incidental information (keywords indicating symptoms) incidental to a dialogue act type in the acquired interactive act and performs search processing for searching through the knowledge base 206 according to a list of the keywords. The knowledge processor 207 determines whether diseases of search targets are sufficiently narrowed down as a result of the search processing. If the diseases of the search targets are sufficiently narrowed down, the knowledge processor 207 returns narrowed-down information (a disease) of the search target to the agent 2001 as a conclusion. If the knowledge processor 207 determines that the narrow-down is insufficient, the knowledge processor 207 proposes (provides) search keywords effective for narrowing down the search targets to the agent 2001. Note that the processing for identifying diseases by the backend 2005 is only an example of information processing by the backend 2005. The information processing performed by the backend 2005 may be, for example, processing for performing, using keywords, an Internet search (a search for information on the Internet), proposing (providing) the next effective search keywords until results of the search are equal to or smaller than a predetermined number (e.g., one or several results), and, when the results of the search are equal to or smaller than the predetermined number, providing information as the result of the search. In this case, the backend 2005 can include a wrapper to an existing Internet search program.

A sequence of interaction by the interactive system 10 is explained below. FIG. 5 is a sequence chart showing an example of a sequence of interaction by the interactive system 10.

In FIG. 5, processing sections (active sections) in the frontend 2002, the agent 2001, and the backend 2005 (objects) are respectively represented by vertically long rectangles. Vertical broken lines downward from the objects represent an elapsed time. Among horizontal arrow lines (arrows), arrows of solid lines represent call messages (i.e., provision of a dialogue act from the agent 2001). Broken line arrows represent result notification messages of procedures (i.e., acquisition of a dialogue act by the agent 2001). In FIG. 5, contents (a list of search keywords) of a stack 50 managed in the backend 2005 are appended. A positive (+) sign added to a keyword in the stack 50 means that the keyword is treated as a designated keyword during the search of the knowledge base 206. A minus (−) sign added to a keyword means that the keyword is treated as an excluded keyword during the search of the knowledge base 206.

Steps in the sequence related to an example of interaction related to a medical interview task are explained in order with reference to FIG. 5.

In step S101, the agent 2001 gives (provides), to the backend 2005, a dialogue act "clear ( )" representing a command for emptying the stack 50 in which search keywords for the search processing of the knowledge base 206 are stored. Note that, if a leading character of the dialogue act provided by the agent 2001 is a lower case letter, the backend 2005 is decided as a providing destination. If the leading character of the dialogue act is an upper case letter, the frontend 2002 is decided as the providing destination.

In step S102, the agent 2001 receives (acquires), from the backend 2005, a dialogue act "pass ( )" indicating that, for example, processing corresponding to the command has ended.

In step S103, the agent 2001 provides a dialogue act "What1st ( )" representing a question "What is the matter with you today?" to the frontend 2002. Consequently, the frontend 2002 questions the user with, for example, a natural language "What is the matter with you today?". In this example, the user answers the question with "I feel dizzy" indicating a symptom.

In step S104, the agent 2001 acquires, from the frontend 2002, a dialogue act "Provide (headache)" obtained by converting the answer "I feel dizzy" of the user in the frontend 2002.

Subsequent to step S104, the agent 2001 determines a dialogue act type "Confirm" according to the dialogue act type "Provide" in the acquired interactive act "Provide (headache)" and combines the "Confirm" and "headache", which is incidental information in the acquired interactive act, to generate a dialogue act for provision "Confirm (headache)".

In step S105, the agent 2001 provides the dialogue act "Confirm (headache)" to the frontend 2002. Consequently, the frontend 2002 questions the user about confirmation with a natural language "Do you have a headache?" converted based on the dialogue act "Confirm (headache)". In this example, in response to the question, the user corrects the headache and answers "I have dizziness".

In step S106, the agent 2001 acquires, from the frontend 2002, a dialogue act "Correct (dizziness)" obtained by converting the answer "I have dizziness" of the user (i.e., an answer for correcting confirmation content) in the frontend 2002.

Subsequent to step S106, the agent 2001 determines a dialogue act type "push" according to the dialogue act type "Correct" in the acquired interactive act "Correct (dizziness). The agent 2001 combines the "push" and "dizziness", which is incidental information in the acquired interactive act, to generate a dialogue act for provision "push (dizziness)".

In step S107, the agent 2001 provides the dialogue act "push (dizziness") to the backend 2005. A designated keyword indicating the incidental information "dizziness" is accumulated in the stack 50 of the backend 2005 according to a command (e.g., a command for setting of search keywords) represented by the dialogue act "push (dizziness)".

In step S108, the agent 2001 acquires, from the backend 2005, a dialogue act "pass ( )" indicating that, for example, the processing corresponding to the commands has ended.

Subsequent to step S108, the agent 2001 determines a dialogue act type "WhatElse" according to a dialogue act type "pass" in the acquired interactive act "pass ( )" and generates a dialogue act "WhatElse ( )".

In step S109, the agent 2001 provides the dialogue act "WhatElse ( )" to the frontend 2002. Note that, in the agent 2001, the belief state referred to in the determination of the dialogue act type changes according to series of interactive act types in sequentially acquired interactive acts. Therefore, even when interactive acts having the same content are acquired, different interactive acts for provision can be determined and provided. The frontend 2002 further questions the user with a natural language "Do you have any other concern?" converted based on the dialogue act "WhatElse ( )". In this example, the user answers the question with "I have palpitations as well" indicating a further symptom.

In step S110, the agent 2001 acquires, from the frontend 2002, a dialogue act "Provide (palpitation)" obtained by converting the answer "I have palpitations as well" of the user in the frontend 2002.

Subsequent to step S110, the agent 2001 determines a dialogue act type "push" according to a dialogue act type "Provide" in the acquired interactive act "Provide (palpitation)" and combines the "push" and "palpitation", which is incidental information in the acquired interactive act, to generate a dialogue act for provision "push (palpitation)".

In step S111, the agent 2001 provides the dialogue act "push "palpitation") to the backend 2005. A designated keyword indicating the incidental information "palpitate" is further accumulated in the stack 50 of the backend 2005 according to a command (e.g., a command for setting of a search keyword) represented by the dialogue act "push (palpitation)".

In step S112, the agent 2001 acquires, from the backend 2005, a dialogue act "pass ( )" indicating that, for example, the processing corresponding to the command has ended.

Subsequent to step S112, the agent 2001 determines a dialogue act type "WhatElse" according to a dialogue act type "pass" in the acquired interactive act "pass ( )" and generates a dialogue act "WhatElse ( )".

In step S113, the agent 2001 provides the dialogue act "WhatElse( )" to the frontend 2002. The frontend 2002 further questions the user with a natural language "Do you have any other concern?" converted based on the dialogue act "WhatElse ( )". In this example, the user answers the question with "No, I don't" indicating that the user does not have other symptoms.

In step S114, the agent 2001 acquires, from the frontend 2002, a dialogue act "Negative ( )" obtained by converting the answer "No, I don't" of the user in the frontend 2002.

Subsequent to step S114, the agent 2001 determines a dialogue act type "solve1st" according to a dialogue act type "Negative" in the acquired interactive act "Negative ( )" and generates a dialogue act for provision "solve1st ( )".

In step S115, the agent 2001 provides the dialogue act "solve1st ( )" to the backend 2005. The backend 2005 performs search processing of the knowledge base 206 according to a command (e.g., a command for search execution) represented by the dialogue act "solve1st ( )". The backend 2005 determines whether results of the search processing are sufficiently narrowed down. For example, the backend 2005 determines whether diseases serving as the results of the search processing are narrowed down to a predetermine number (e.g., one or several diseases). If the results of the search processing are not sufficiently narrowed down, the backend 2005 identifies and proposes, using the knowledge base 206, search keywords effective for narrowing down the results of the search processing. In this processing, the results of the search processing are not narrowed down to the predetermined number or less. "Fever" is proposed as a search keyword effective for the narrow-down. At this point, in this example, a search keyword indicating "fever" in a state in which it is not determined whether the search keyword is a designated keyword or an excluded keyword is accumulated.

In step S116, the agent 2001 acquires, from the backend 2005, a dialogue act "suggest (fever)" indicating that a question of a symptom of "fever" is proposed.

Following step S116, the agent 2001 determines a dialogue act type "Check" according to a dialogue act type "suggest" in the acquired interactive act "suggest (fever)" and combines the "Check" and the "fever", which is incidental information in the acquired interactive act, to generate a dialogue act for provision "Check (fever)".

In step S117, the agent 2001 provides the dialogue act "Check (fever)" to the frontend 2002. The frontend 2002 questions the user about a symptom of fever with a natural language "Do you have fever?" converted based on the dialogue act "Check (fever)". In this example, the user answers the question with "No, I don't" indicating that the symptom of the fever does not appear.

In step S118, the agent 2001 acquires, from the frontend 2002, a dialogue act "Negative ( )" obtained by converting the answer "No, I don't" of the user in the frontend 2002.

Subsequent to step S118, the agent 2001 determines a dialogue act type "set_negative" according to a dialogue act type "Negative" in the acquired interactive act "Negative ( )" and generates a dialogue act for provision "set_negative ( )".

In step S119, the agent 2001 provides the dialogue act "set_negative ( )" to the backend 2005. According to a command represented by the dialogue act "set_negative ( )" (e.g., a command for executing a search in a list of search keywords after setting a search keyword stacked last in a stack as an excluded keyword), the backend 2005 performs search processing of the knowledge base 206 using "fever" of the stack 50 as an excluded keyword. The backend 2005 determines whether results of the search processing are sufficiently narrowed down. In this example, the results of the search processing are not narrowed down to the predetermined number or less yes. "Cough" is further proposed as a search keyword effective for the narrow-down. At this point, in this example, a search keyword indicating "cough" is accumulated in the stack 50 of the backend 2005.

In step S120, the agent 2001 acquires, from the backend 2005, a dialogue act "suggest (cough)" indicating that a question of a symptom of "cough" is proposed.

Subsequent to step S120, the agent 2001 determines a dialogue act type "Check" according to a dialogue act type "suggest" in the acquired interactive act "suggest (cough)" and combines the "Check" and the "cough", which is incidental information in the acquired interactive act, to generate a dialogue act for provision "Check (cough)".

In step S121, the agent 2001 provides the dialogue act "Check (cough)" to the frontend 2002. The frontend 2002 questions the user about a symptom of cough with a natural language "Do you cough?" converted based on the dialogue act "Check (cough)". In this example, the user answers the question with "Yes, I do" indicating that the symptom of the cough appears.

In step S122, the agent 2001 acquires, from the frontend 2002, a dialogue act "Positive ( )" obtained by converting the answer "Yes, I do" of the user in the frontend 2002.

Subsequent to step S122, the agent 2001 determines a dialogue act type "set_positive" according to a dialogue act type "Positive" in the acquired interactive act "Positive ( )" and generates a dialogue act for provision "set_positive ( )".

In step S123, the agent 2001 provides the dialogue act "set_positive ( )" to the backend 2005. According to a command represented by the dialogue act "set_positive ( )" (e.g., a command for executing a search in a list of search keywords after setting a search keyword stacked last in a stack as a designated keyword), the backend 2005 performs search processing of the knowledge base 206 using "cough" of the stack 50 as a designated keyword. The backend 2005 determines whether results of the search processing are sufficiently narrowed down. In this example, the results of the search processing are narrowed down to the "disease C", which is one result equal to or smaller than the predetermined number.

In step S124, the agent 2001 acquires, from the backend 2005, a dialogue act "conclude (disease C)" representing the "disease C" serving as a conclusion.

Subsequent to step S124, the agent 2001 determines a dialogue act type "Present" according to a dialogue act type "conclude" in the acquired interactive act "conclude (disease C)" and combines the "Present" and the "disease C", which is incidental information in the acquired interactive act, to generate a dialogue act for provision "Present (disease C)".

In step S125, the agent 2001 provides the dialogue act "Present (disease C)" to the frontend 2002. The frontend 2002 provides a conclusion to the user with a natural language "You seem to have the disease C" converted based on the dialogue act "Present (disease C)". In this example, the user answers the provision of the conclusion with "I see".

In step S126, the agent 2001 acquires, from the frontend 2002, a dialogue act "Acknowledge ( )" obtained by converting the answer "I see" of the user in the frontend 2002. Consequently, the agent 2001 ends the interactive processing and the sequence of the interaction has ended.

In this way, the interaction between the frontend 2002 and the backend 2005 is performed through the mediation by the agent 2001.

In the example explained above, a sequence of the dialogue act, which is the information exchanged between the agent 2001 and the frontend 2002, is a dialogue act sequence 1 described below.

The dialogue act sequence 1=[What1st ( ), Provide (headache), Confirm (headache), Correct (dizziness), WhatElse ( ), Provide (palpitation), WhatElse ( ), Negative ( ), Check (fever), Negative ( ), Check (cough), Positive ( ), Present (disease C), Acknowledge ( )]

A sequence obtained by adding the dialogue act exchanged between the agent 2001 and the backend 2005 to the dialogue act sequence 1 is a dialogue act sequence 2 described below.

The dialogue act sequence 2=[clear ( ), pass ( ), What1st ( ), Provide (headache), Confirm (headache), Correct (dizziness), push (dizziness), pass ( ) WhatElse ( ), Provide (palpitation), push (palpitation), pass ( ), WhatElse ( ), Negative ( ), solve1st ( ), suggest (fever), Check (fever), Negative ( ), set_negative ( ), suggest (cough), Check (cough), Positive ( ), set_positive ( ), conclude (disease C), Present (disease C), Acknowledge ( )]

In the dialogue act sequence 2, an odd number-th interactive act corresponds to an action of the agent 2001. An even number-th interactive act corresponds to an observation obtained by the agent 2001 from the frontend 2002 or the backend 2005 serving as the environment. When focusing on the incidental information in the parentheses, the incidental information coincides between the observation and the following action. That is, although the agent 2001 (the interactive agent) determines the dialogue act types such as Conform for Provide and push for Correct, the agent 2001 simply mediates concerning the incidental information. Such an operation for determining an action according to an observation is realized by the determiner 200 (i.e., the separator 202, the action determiner 203, and the combiner 204) of the agent 2001.

(Discussion Concerning an Interaction State)

For example, a reduction of the number of interaction states transitioning in the interaction by the interactive system 10 is discussed below with reference to FIGS. 6A to 6D.

First, an interactive system including only a frontend related to the user as an environment is assumed using the dialogue act sequence 1 related to the example shown in FIG. 5. An example of interaction between the frontend and an agent (a system including a function of knowledge processing) in the assumed interactive system is examined.

Figure 6A:
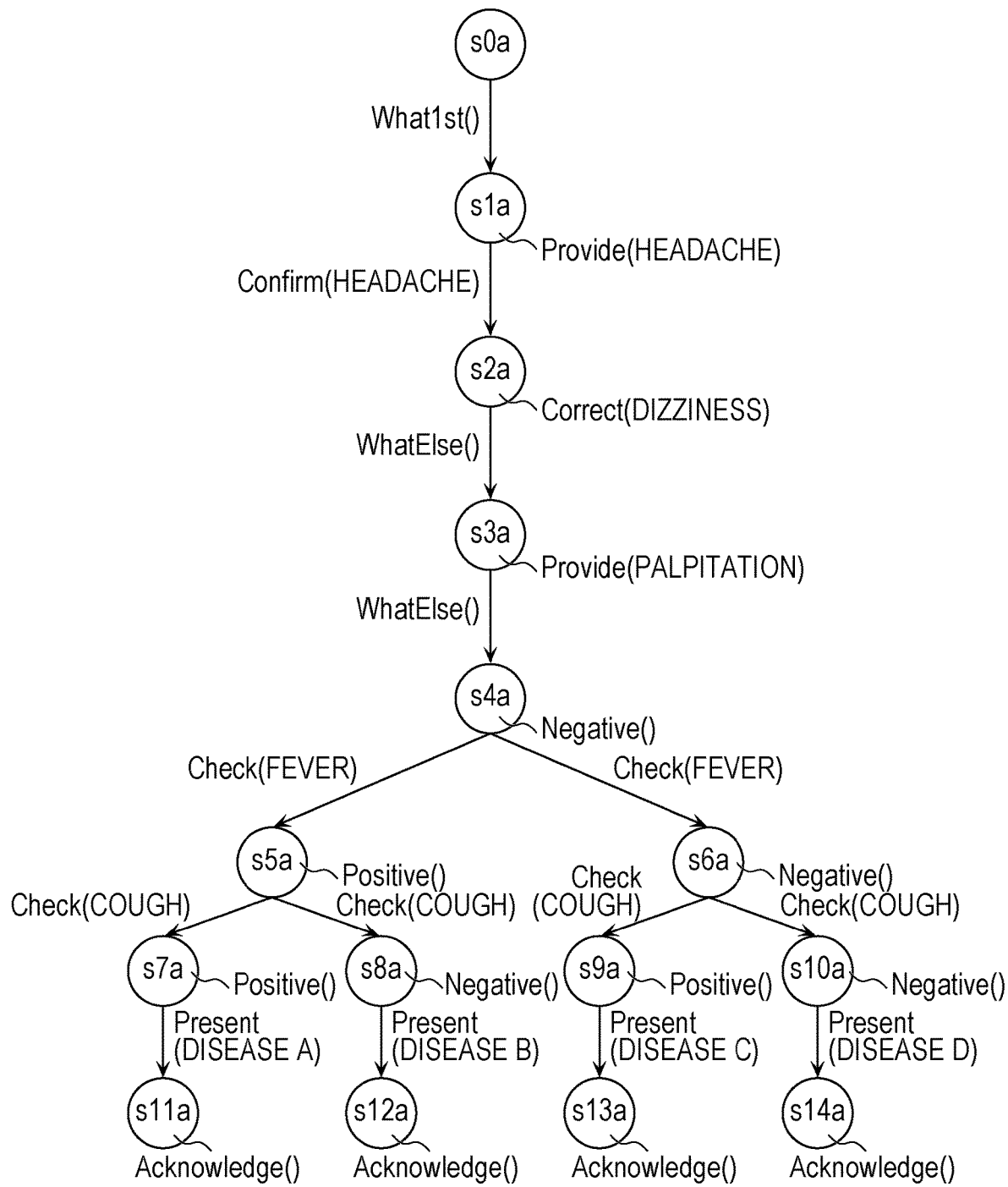
FIG. 6A is a state transition chart (No. 1) concerning an interaction state.

FIG. 6A is a state transition chart showing an example of a state transition created to include the dialogue act sequence 1. Note that, in the POMDP model, a relation among an action, an observation, and state is represented by a transition probability $T(s'|s, a)$ at the time when a state transition to "s'" if an action "a" is taken when the state is "s" and an observation probability $O(z|a, s')$ that an observation "z" is obtained in the state "s'" as a result of taking the action "a". The probabilities in the POMDP model are subjected to threshold processing. The relation among the action, the observation, and the state is represented by a state transition chart. State transition charts shown in FIGS. 6B to 6D referred to below are the same as FIG. 6A. For example, arrow lines in the state transition chart represent routes in which transition probabilities of states exceed fixed thresholds. In FIGS. 6A to 6D, names of states are written in circles representing nodes. Interactive acts serving as acts from the agent to the environment are written in arrow lines representing edges among the nodes. Interactive acts serving as observations of the environment by the agent are written in the nodes (states). Consequently, the state transition chart indicates that a state of the environment changes according to the actions and the observation is performed under the changed state.

The dialogue act sequence 1 is divided into two portions (parts) and discussed. First, a part of [What1st ( ), Provide (headache), Confirm (headache), Correct (dizziness), WhatElse ( ), Provide (palpitation), WhatElse ( ), Negative ( )], which is a preceding part, is a part in which user-centered interaction mainly for an open question is performed. This part is called patient-centric medical interview in a medical interview task. On the other hand, a part of [Check (fever), Negative ( ), Check (cough), Positive ( ), Present (disease C), Acknowledge ( )], which is a following part, is a part in which system-centered interaction mainly for a closed question is performed. This part is called doctor-centric medical interview in the medical interview task.

Concerning the preceding part (the user-centered interaction part), in FIG. 6A, states (nodes) of the part are linearly arranged. A sequence of a dialogue act corresponding to the part is a variable-length sequence ending with an observation Negative ( ). In order to reduce the number of states in the part, it seems sufficient to degenerate "s1a" to "s3a" to form a loop structure. It is possible to cope with the variable-length sequence with the loop.

Concerning the following part (the system-based interaction part), in FIG. 6A, states (nodes) of the part are arranged to form a tree structure. In order to trace the system-based interaction part of the dialogue act sequence 1, routes of series of states [s6a, s9a, s13a] only have to be tracked following "s4a". The part of the tree structure as a whole corresponds to the question tree illustrated in FIG. 4B. It is possible to reach different conclusions following questions and answers. The system-based interaction part can increase according to, for example, a size of a knowledge base. That is, if there are one thousand conclusions, the number of states is one thousand or more. In the question tree shown in FIG. 4B, the lengths of the routes are the same because the question tree is a simple example. However, the lengths of the routes of the system-based interaction part are variable lengths. It seems that the part is desirably formed in a loop structure.

Figure 6B:
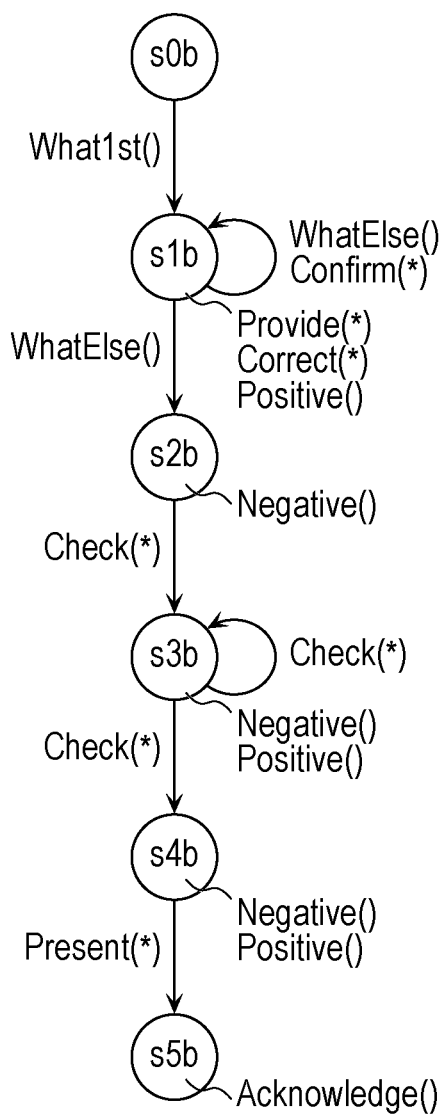
FIG. 6B is a state transition chart (No. 2) concerning the interaction state.

FIG. 6B is a state transition chart showing an example of a state transition formed to have two loop structures based on the above discussion.

Like FIG. 6A, FIG. 6B corresponds to the user-centered interaction part [What1st ( ), Provide (headache), Confirm (headache), Correct (dizziness), WhatElse ( ), Provide (palpitation), WhatElse ( ), Negative ( )] and the system-based interaction part [Check (fever), Negative ( ), Check (cough), Positive ( ), Present (disease C), Acknowledge ( )] of the dialogue act sequence 1. However, in FIG. 6B, the "headache", the "disease C", and the like, which are the incidental information of the dialogue acts, are generalized and represented by "*". In any case, the incidental information of the generalized portion has the same correspondence relation with the states.

When focusing on a state "s1 b" in FIG. 6B, the next state is "s1b" or "s2b". That is, after rounding a loop for leaving "s1b" and returning to "s1b" zero times or more, the state transition leaves the loop and proceeds to "s2b". Different observations are written in "s1b" and "s2b". When a dialogue act "Negative ( )" is observed with respect to a dialogue act "WhatElse ( )" serving as an action, the state transition leaves the loop.

When focusing on a state "s3b", the next state is "s3b" or "s4b". That is, after rounding a loop for leaving "s3b" and returning to "s3b" zero times or more, the state transition leaves the loop and proceeds to "s4b". The same observations ("Negative ( )" and "Positive ( )") are written in "s3b" and "s4b". An action "Check (*)" is also the same. Therefore, a condition for leaving the loop is unclear. In such a case, it is determined, according to a ratio of a transition probability of rounding the loop and a transition probability of leaving the loop, how many times the loop is rounded to leave the loop. However, if a medical interview task of identifying a disease through a medical interview is considered, the doctor should determine an end of the loop according to content of the medical interview. The end should not be determined according to the number of times. Alternatively, the state transition may proceed from "s3b" to "s5b" excluding "s4b" according to an action "Present (*)" (not shown in FIG. 6B). However, there is no information for action selection. Even if determination concerning whether to round the loop according to the action "Check (*)" or leave the loop according to the action "Present (*)" follows a policy obtained by reinforcement learning, if states and observations are the same, the same action is always selected. That is, the state transition can only enter an endless loop or pass the loop without rounding the loop at all. This occurs when only the frontend related to the user is set as the environment and states are degenerated as much as possible without using the incidental information of the dialogue acts. This makes it impossible to carry out the task.

The interactive system 10 in which the frontend 2002 and the backend 2005 are respectively set as environments are examined using the dialogue act sequence 2 related to the example shown in FIG. 5.

Figure 6C:
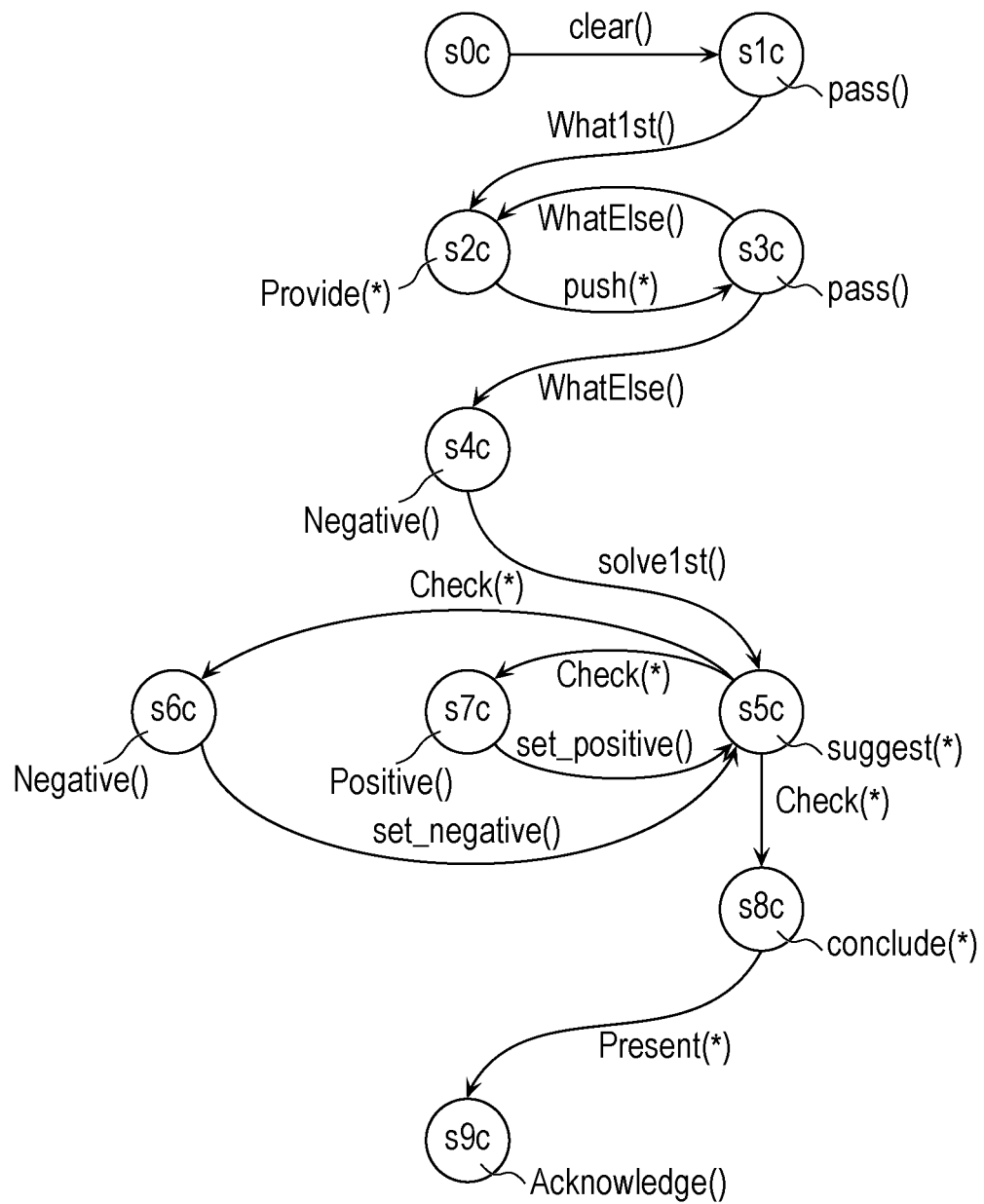
FIG. 6C is a state transition chart (No. 3) concerning the interaction state.

FIG. 6C is a state transition chart showing an example of a state transition created according to the dialogue act sequence 2. The state transition chart of FIG. 6C includes two loop structures and is adapted to two environments.

Throughout the entire interactive act sequence 2, FIGS. 6B and 6C are the same in that the two loops are present. In FIG. 6C, concerning arrangement of nodes, the nodes are arranged such that the left side corresponds to interactive acts exchanged between the frontend 2002 and the agent 2001 and the right side corresponds to interactive acts exchanged between the agent 2001 and the backend 2005.

As in the dialogue act sequence 1 explained above, the dialogue act sequence 2 is divided into two portions (parts) and examined. That is, the dialogue act sequence 2 is divided into a part of [clear ( ), pass ( ), What1st ( ), Provide (headache), Confirm (headache), Correct (dizziness), push (dizziness), pass ( ), WhatElse ( ), Provide (palpitation), push (palpitation), pass ( ), WhatElse ( ), Negative ( )], which is a user-based interactive part, and a part of [solve1st ( ), suggest (fever), Check (fever), Negative ( ), set_negative ( ), suggest (cough), Check (cough), Positive ( ), set_positive ( ), conclude (disease C), Present (disease C), Acknowledge ( )], which is a system-based interactive part following the user-based interactive part.

In the user-based interactive part shown in FIG. 6C, a first loop is present. An end condition of the loop is given by an observation (specifically, "Negative ( )") from the frontend 2002. The end condition of the first loop is the same as the end condition of the first loop shown in FIG. 6B. On the other hand, in the system-based interactive part shown in FIG. 6C, a second loop is present. An end condition of the loop is given by an observation (specifically, "conclude (*)" from the backend 2005. To supplement, an action that should be taken in "s5c" is "Check (*)" and there are three transition destinations of "s5c". A state is set for each of observations assumed next. Therefore, when the state is multiplied with an observation probability, a probability of the state corresponding to the observation increases. That is, an end condition of the second loop is different from the end condition shown in FIG. 6B. The state of the dialogue act given as the observation is reflected on the probability and can be a reference of action determination. Therefore, it is possible to acquire an appropriate policy through reinforcement learning.

Note that, in a first loop in FIG. 6C, a state transition corresponding to a sequence [Confirm (headache), Correct (dizziness)] is omitted. This is discussed with reference to FIG. 6D.

Figure 6D:
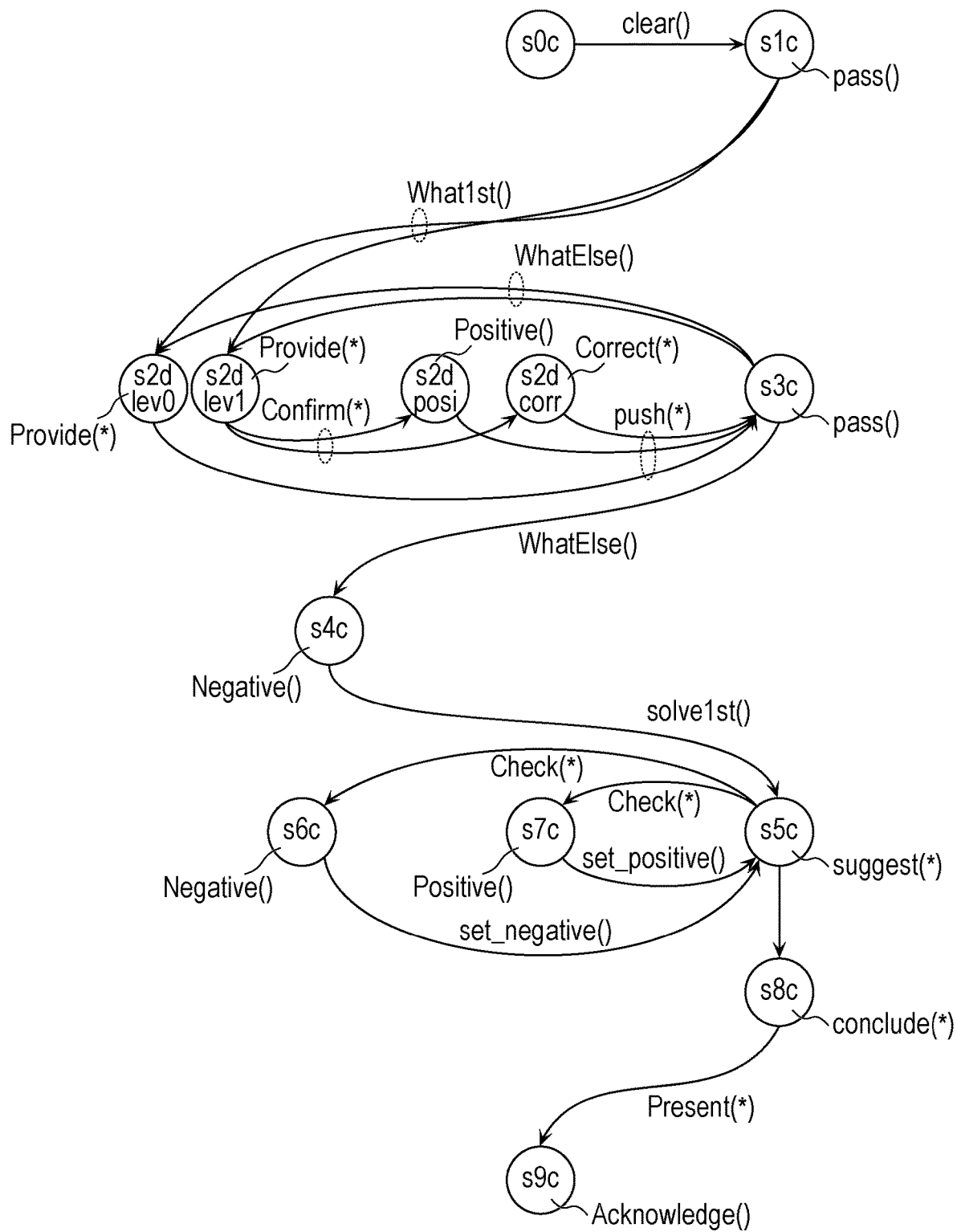
FIG. 6D is a state transition chart (No. 4) concerning the interaction state.

FIG. 6D is a state transition chart showing a state transition in which a state of "s2c" in FIG. 6C is divided and expansion for coping with uncertainty is performed. In FIG. 6D, nodes excluding four nodes of "s2d lev0", "s2d lev1", "s2d posi", and "s2d corr" correspond to nodes having the same names in FIG. 6C.

First expansion is division of a state corresponding to the reliability of a result of language understanding obtained from the input processor 201 of the frontend 2002. The nodes of "s2d lev0" and "s2d lev1" are divided according to magnitude comparison with a threshold of reliability set in advance. The node having reliability larger than the threshold is "s2d lev0". The node having reliability smaller than the threshold is "s2d lev1". In this example, the state is divided into two. However, the number of divisions only has to be increased to approximately several times according to necessity. Examples of a way of setting thresholds in the case of a division into four include a method of setting threshold to equally divide a value range that the reliability can take into four and a method of obtaining a frequency distribution and setting quartiles as thresholds.

Second expansion is provision of states "s2d posi" and "s2d corr" corresponding to improving certainty by confirming with the frontend 2002 before the agent 2001 mediates information obtained from the frontend 2002 to the backend 2005.

When a state of the state transition is tracked according to a portion of [Provide (headache), Confirm (headache), Correct (dizziness), push (dizziness), pass ( ), WhatElse ( ), Provide (palpitation), push (palpitation)] of the dialogue act sequence 2, when reliability at the time when "Provide (headache)" is observed is relatively low, it is assumed that the state transition is in the state "s2d lev1". An action of "Confirm (headache)" is determined, the state transitions to "s2d corr", and "Correct (dizziness)" is observed. Subsequently, an action of "push (dizziness)" is determined, the state transitions to "s3c", and "pass ( )" is observed. Subsequently, an action of "WhatElse ( )" is determined and "Provide (palpitation)" is observed together with relatively high reliability. Then, it is assumed that the state transition is in "s2d lev0". The state is transitioned to "s3c" while involving an action "push (palpitation)" without being confirmed.

In this way, the state can be divided based on the reliability of the observation from the frontend 2002. Separate actions can be linked to each of the divided states. In the example shown in FIG. 6D, levels of reliability (i.e., the number of divisions by thresholds) are two. The confirmation is not performed when the reliability is high. The confirmation is performed when the reliability is low. If the levels of reliability are two levels, it is easy to manually set a policy for deciding an action corresponding to the reliability. When levels of reliability are set in multiple stages, trial and error are necessary for setting for each of the levels whether the confirmation is performed.

Note that, in the explanation concerning the example shown in FIG. 5, concerning the dialogue act sequence 2, the incidental information coincides between the dialogue act of the observation and the dialogue act of the action following the dialogue act of the observation. However, in FIG. 6D, in a route of "s2d lev1, s2d posi, s3c", for example, a state transition corresponding to a sequence of [Provide (headache), Confirm (headache), Positive ( ), push (headache)] is also possible. As explained above, concerning the incidental information separated from the dialogue act type in the acquired interactive act, acquired latest one kind of incidental information is retained. Therefore, it is possible to cope with the state transition shown in FIG. 6D by adding the retained latest incidental information as a dialogue act of an action according to necessity.

(Comparative Experiment Result)

A comparative experiment for quantitatively showing an effect of the interactive system 10 is explained below.

Figures 7, 8:
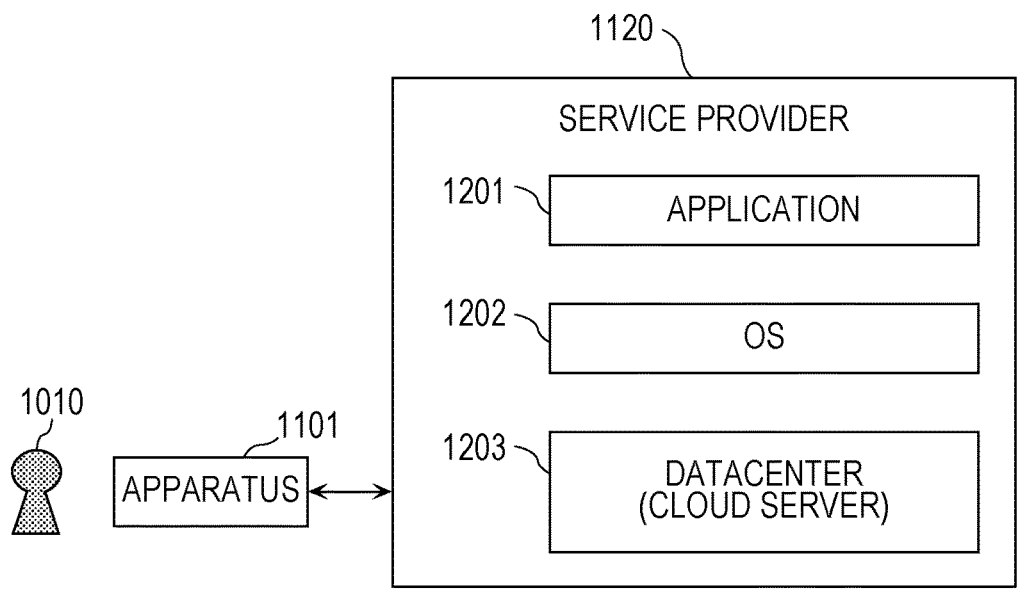
FIG. 7 is a diagram showing a result of an experiment performed using the interactive system according to the embodiment.
FIG. 8 is a conceptual diagram showing a service (a type 1) provided by the interactive system.

A simulation experiment of interaction serving as a medical interview task was performed using the interactive system 10. FIG. 7 is a diagram showing a result of the simulation experiment performed by using the interactive system 10.

In this simulation experiment, as the knowledge base 206, a knowledge base storing a relation between thirty-nine types of symptoms and eight hundred fifty-four diseases was used. As interactive act types, the dialogue act types in the dialogue acts included in the observation 2003, the observation 2006, the action 2004, and the action 2007 (see FIG. 2) were used. A patient simulator acting as the user interacting with the frontend 2002 of the interactive system 10 in the simulation experiment of the interaction performs an answer of a symptom (an answer equivalent to the dialogue act [Provide ( )]) associated with a designated disease once. Thereafter, the patient simulator responds to questions of the interactive system 10.

Other main conditions are as explained below.

A functional portion of language understanding in the frontend 2002 generates a symptom that is wrong at a rate of 25%.

The number of divisions of a state corresponding to reliability is four and three thresholds for the division are 0.2, 0.5, and 0.8.

If a disease (a candidate of a disease) identified by performing a search using a search keyword related to a symptom is one or there is no candidate of a keyword (a symptom) for narrowing down diseases, the backend 2005 (the knowledge processor 207) outputs the disease identified by the search as a conclusion (provides the conclusion to the agent 2001). Otherwise, the backend 2005 proposes a keyword effective for narrowing down the diseases (provides the keyword to the agent 2001).

If the number of diseases obtained as the conclusion is three or less and a disease designated to the patient simulator is included in the diseases, it is determined that the conclusion is correct.

In FIG. 7, experiment results in three types of models of "confirmation strategy is absent", "confirmation strategy is present (hand-crafted)", and "confirmation strategy is present (reinforcement learning)" are summarized under the conditions explained above. The "confirmation strategy is absent" is a model corresponding to the state transition chart of FIG. 6C. The "confirmation strategy is present (hand-crafted)" is a model for not performing confirmation concerning two states in which reliability is 0.5 or more and performing confirmation concerning two states in which reliability is less than 0.5 and is a model corresponding to the state transition chart of FIG. 6D. The "confirmation strategy is present (reinforcement learning)" is also a model equivalent to the type of the state transition chart of FIG. 6D. However, in this model, whether actions that should be taken in the four states corresponding to reliability is "pushed" after being confirmed or is "pushed" without being confirmed conforms to a policy obtained by the reinforcement learning in the POMDP model. Whereas the agent observes, in a certain environment, a present state and determines an action that should be taken, in the reinforcement learning, the agent performs sequentially selected actions to learn a policy in which largest rewards can be obtained from the environment. Concerning a reward in the reinforcement learning of the model of the "confirmation strategy is present (reinforcement learning)", 5 was set as a base concerning a route in which a series of a dialogue act appearing in an interactive corpus passes and −50 was set as a base concerning other routes. In particular, "push (*)" from "s2d corr" was set to 100 and "push (*)" from "s2d posi" was set to −1. A value of confirmation was set high if confirmation for error correction was performed and an error was corrected and set low when correction was unnecessary.

An average number of turns shown in FIG. 7 is the number of turns counted concerning only interaction between the frontend 2002 and the user (the patient simulator). An average reward is calculated under the same condition concerning a model not using the reinforcement learning besides the "confirmation strategy is present (reinforcement learning)".

As an experiment result, as shown in FIG. 7, it was confirmed that the correct answer rate is the highest in the "confirmation strategy is present (reinforcement learning)", the second highest in the "confirmation strategy is present (hand-crafted)", and the lowest in the "confirmation strategy is absent". It was confirmed that the average number of turns is the smallest in the "confirmation strategy is present (reinforcement learning)", the next smallest in the "confirmation strategy is present (hand-crafted)", and the largest in the "confirmation strategy is absent". It was confirmed that the average reward to be obtained is the highest in the "confirmation strategy is present (reinforcement learning)", the second highest in the "confirmation strategy is present (hand-crafted)", and the lowest in the "confirmation strategy is absent".

Note that a time required until a learning result by a POMDP solver used for the reinforcement learning of the model of the "confirmation strategy is present (reinforcement learning)" converges is less than one second. However, in the model corresponding to the state transition chart of FIG. 6A, a time required by the POMDP solver is 30 days or more.

(Other Embodiments and the Like)

As explained above, the first embodiment is used for the explanation as the illustration of the technique according to the present disclosure. However, the embodiment is only an example. It goes without saying that various changes, additions, omissions, and the like are possible.

In the embodiment, the example is explained in which the backend 2005 performs the search processing of the knowledge base 206. However, the information processing in the backend 2005 does not have to be the search processing and may be any processing. The backend 2005 may communicate with an external apparatus other than the knowledge base 206. The knowledge base 206 does not always need to be present on the outside of the backend 2005 and may be included in the backend 2005.

In the embodiment, the example is explained in which one frontend 2002 and one backend 2005 are provided. However, a plurality of frontends 2002 and a plurality of backends 2005 may be provided.

In the embodiment, the example is explained in which the incidental information is the keyword. However, the incidental information may be information other than the character string. For example, the incidental information may be a mark, a figure, an image, sound data, or the like. For example, the incidental information is not limited to only the keyword but may be a set of the keyword and a slot representing a type of the keyword.

In the embodiment, the action determiner 203 determines the dialogue act type as the action based on the POMDP model. However, the action determiner 203 does not always have to be based on the POMDP model. The action determiner 203 may determine the dialogue act type, for example, without depending on the belief state, based on a policy decided in advance and a series (a history) of interactive act types input in the past.

In the embodiment, the example is explained in which the provider 205 determines according to the leading character in the dialogue act is the upper case letter or the lower case letter whether the providing destination of the dialogue act is the frontend 2002 or the backend 2005. However, the providing destination of the dialogue act only has to be distinguished according to whether a value of a dialogue act type (a dialogue act type value) in the dialogue act is a type (a first type) decided in advance as a type directed to the frontend 2002 or a type (a second type) decided in advance as a type directed to the backend 2005. Therefore, the distinction may be realized by a method other than the distinction by the upper case letter and the lower case letter. The provider 205 may include a correspondence table in which the dialogue act type value and the first type and the second type (i.e., the types for distinguishing the providing destination) are associated. For example, the provider 205 can select the providing destination of the dialogue act based on which of interactive act type values of the first type and the second type the dialogue act type in the dialogue act for provision determined by the determiner 200 represents and provide the dialogue act to the selected providing destination.

In the embodiment, the example is explained in which the interactive system 10 is used for the medical interview. However, the dialogue act type is not limited to the medical interview and is common in a task of identifying information through interaction.

Therefore, the interactive system 10 is not limited to the example of the medical interview and can be applied to performance of a task of identifying information through interaction with a user. As a specific example, the interactive system 10 can be applied to a recipe search in the field of cooking or the like, a travel plan search in the field of sightseeing or the like, a real estate property search in the field of real estate transaction or the like, a video content search in the field of a television broadcast or the like. In this case, in the interactive system 10 (see FIG. 2), for example, information useful in a predetermined field (an application field of the interactive system 10, etc.) only has to be retained in the knowledge base 206. The frontend 2002 only has to exchange information expressed in a natural language concerning the field with the user. Note that interactive processing performed by the interactive system 10 is the same as the processing illustrated in FIG. 3.

When the interactive system 10 is used for the recipe search, for example, information related to food materials, seasonings, dishes, cooking methods, and the like only has to be retained in the knowledge base 206. The frontend 2002 only has to acquire, for example, information concerning a genre, food materials, and the like of a favorite dish through interaction with a user. When the interactive system 10 is used for the travel plan search, for example, information concerning destinations, the numbers of people, the numbers of nights, estimates of expenses, and the like only has to be retained in the knowledge base 206. The frontend 2002 only has to acquire, for example, information concerning a destination, the number of people, and the like of a travel plan desired by a user through interaction with the user. When the interactive system 10 is used for the real estate property search, for example, information related to residence areas, room layouts, ages of buildings, distances from closest stations, rents, and the like only has to be retained in the knowledge base 206. The frontend 2002 only has to acquire, for example, information concerning a residence area, a room layout, and the like of a real estate property desired by a user through interaction with the user. When the interactive system 10 is used for the video content search, for example, information concerning genres, performers, broadcasting stations, broadcasting date and times, and the like only has to be retained in the knowledge base 206. The frontend 2002 only has to acquire, for example, information concerning a genre, performers, and the like of a program that a user desires to watch through interaction with the user. Note that, in all the tasks, a type, acquisition order, a total number, and the like of the information acquired from the user through the interaction with the user do not need to be fixed values or the like decided in advance and only have to be dynamically determined to satisfy a condition that information desired by the user is sufficiently narrowed down and identified.

In the examples explained above, the separator 202 in the agent 2001 separates the dialogue act acquired from either one of the frontend 2002 and the backend 2005 into the dialogue act type and the incidental information. However, as explained above, in the task of identifying information, the dialogue act type is common irrespective of fields. Therefore, as a value of the dialogue act type, a value same as the value in the example of the medical interview can be used.

Note that interactive act types may be added as appropriate according to a specific application field. For example, in the recipe search, in addition to the dialogue act types illustrated in the embodiment, in a case in which information concerning a recipe recommended according to an information request from the user (a recommended recipe) is presented, a dialogue act type "RequestRecommend" of a recommended information request from the frontend 2002 to the agent 2001, a dialogue act type "seek_recommend" of a recommended information search from the agent 2001 to the backend 2005, a recommended act type "inform_recommend" of recommended information provision from the backend 2005 to the agent 2001, recommended information presentation "PresentRecommend" from the agent 2001 to the frontend 2002, recommendation information, and the like may be added. In this way, it is possible to efficiently identify information according to a field.

A part or all of the components (the agent 2001, the frontend 2002, the backend 2005, etc.) in the embodiment may be configured from one system LSI (Large Scale Integration). The system LSI is an ultra-multifunction LSI manufactured by integrating a plurality of constituent sections on one chip. Specifically, the system LSI is a computer system configured to include a microprocessor, a ROM, and a RAM. A computer program is recorded in the RAM. The microprocessor operates according to the computer program, whereby the system LSI achieves a function of the system LSI. The sections of the components of the apparatuses may be individually formed as one chip or may be formed as one chip to include a part or all of the sections. Although the system LSI is referred to above, the system LSI is sometimes called IC, LSI, super LSI, or ultra LSI according to a difference in a degree of integration. A method of conversion into an integrated circuit is not limited to the LSI and may be realized by a dedicated circuit or a general-purpose processor. After LSI manufacturing, a programmable FPGA (Field Programmable Gate Array) or a reconfigurable processor capable of reconfiguring connection and setting of circuit cells inside the LSI may be used. Further, if a technique for conversion into an integrated circuit replacing the LSI appears according to progress of the semiconductor technique or another technique deriving from the semiconductor technique, naturally, integration of functional blocks may be performed using the technique. For example, application of the biotechnology is possible.

A part of all of the components in the embodiment may be configured from an IC card or a single module detachably attachable to an apparatus such as a computer. The IC card or the module is a computer system configured from a microprocessor, a ROM, a RAM, and the like. The IC card or the module may include the ultra-multifunction LSI. The microprocessor operates according to a computer program, whereby the IC card or the module achieves a function of the IC card or the module. The IC card or the module may have tamper resistance.

An aspect of the present disclosure may be an interactive method including all or a part of the procedures shown in FIGS. 3 and 5 and the like. The interactive method used in the interactive system 10 includes, for example, a determining step in which the agent 2001 determines a dialogue act for provision according to a dialogue act acquired from one of the frontend 2002 and the backend 2005 and a providing step in which the agent 2001 provides the dialogue act for provision determined in the determining step to one of the frontend 2002 and the backend 2005. In the determining step, the agent 2001 determines a dialogue act type in the dialogue act for provision not based on series of incidental information but based on series of interactive act types in interactive acts sequentially acquired from the set of the frontend 2002 and the backend 2005. For example, the determining step includes a separating sub-step for sequentially acquiring interactive acts from the set of the frontend 2002 and the backend 2005 and separating incidental information and interactive act types in the acquired interactive acts, an action determining sub-step for setting the dialogue act type separated in the separating sub-step as an observation and determining, based on the observation, referring to belief state information serving as a reference for determining an action according to the observation, a dialogue act type serving as an action, a combining sub-step for combining the dialogue act type determined in the action determining sub-step and the incidental information separated in the separating sub-step to generate a dialogue act for provision, and an updating step for updating the belief state information according to an observation, which is a series of the dialogue act type separated in the separating sub-step, and an action, which is a series of the dialogue act type determined in the action determining sub-step. An aspect of the present disclosure may be a computer program for realizing the interactive method using a computer (e.g., a computer program for performing interactive control processing including the determining step and the providing step) or may be a digital signal including the computer program. An aspect of the present disclosure may be a computer-readable recording medium, for example, a flexible disk, a hard disk, a CD-ROM, an MO, a DVD, a DVD-ROM, a DVD-RAM, a BD (Blu-ray (registered trademark) Disc), or a semiconductor memory having the computer program or the digital signal recorded therein. An aspect of the present disclosure may be the digital signal recorded in the recording medium. An aspect of the present disclosure may be the computer program or the digital signal transmitted through an electric communication line, a wireless or wired communication line, a network represented by the Internet, a data broadcast, or the like. An aspect of the present disclosure may be a computer system including a microprocessor and a memory, the memory having the computer program recorded therein and the microprocessor operating according to the computer program. The computer program or the digital signal may be recorded in the recording medium and transferred or the computer program or the digital signal may be transferred through the network or the like to thereby be carried out by independent other computer systems.

The technique related to the interactive system 10 explained in the embodiment can be realized in, for example, types of cloud services explained below besides the form of the service explained above (see FIG. 1). However, the application of the technique explained in the embodiment is not limited to the types of the cloud services explained below.

(Type 1 of a Service: An Own Company Datacenter Type Cloud Service)

FIG. 8 is a diagram showing an overview of a service provided by an interactive system in a type 1 of a service (an own company datacenter type cloud service). In this type, the service provider 1120 acquires information input by the user 1010 from the apparatus 1101 and provides a service to the user 1010 via the apparatus 1101. In this type, the service provider 1120 has a function of a datacenter operation company. That is, the service provider 1120 owns a cloud server that manages big data. In this type, the datacenter operation company is absent. In this type, the service provider 1120 includes a cloud server 1203 functioning as a datacenter and manages an operating system (OS) 1202 and an application program (application) 1201. The service provider 1120 communicates with the apparatus 1101 through the cloud server 1203 using the OS 1202 and the application 1201 to provide the service.

(Type 2 of a Service: An IaaS Use Type Cloud Service)

FIG. 9 is a diagram showing an overview of a service provided by an interactive system in a type 2 of a service (an IaaS use type cloud service). IaaS is an abbreviation of infrastructure as a service. The IaaS use type cloud service is a cloud service provision model for providing, as a service through the Internet, an infrastructure itself for constructing and operating a computer system.

In this type, the datacenter management company 1110 operates and manages the datacenter (cloud server) 1203. The service provider 1120 manages the OS 1202 and the application 1201. The service provider 1120 provides the service using the OS 1202 and the application 1201 managed by the service provider 1120.

(Type 3 of a Service: A PaaS Use Type Cloud Service)

FIG. 10 is a diagram showing an overview of a service provided by an interactive system in a type 3 of a service (a PaaS use type cloud service). PaaS is an abbreviation of platform as a service. The PaaS use type cloud service is a cloud service provision model for providing, as a service through the Internet, a platform functioning as a base for constructing and operating software.

In this type, the datacenter operation company 1110 manages the OS 1202 and operates and manages the datacenter (cloud server) 1203. The service provider 1120 manages the application 1201. The service provider 1120 provides the service using the OS 1202 managed by the datacenter operation company 1110 and the application 1201 managed by the service provider 1120.

(Type 4 of a Service: An SaaS Use Type Cloud Service)

FIG. 11 is a diagram showing an overview of a service provided by an interactive system in a type 4 of a service (an SaaS use type cloud service). SaaS is an abbreviation of software as a service. The SaaS use type cloud service is a cloud service provision model having a function of enabling a user such as a company or an individual not owning a datacenter (a cloud server) to use, through a network such as the Internet, for example, an application provided by a platform provider owning the datacenter (the could server).

In this type, the datacenter operation company 1110 manages the application 1201, manages the OS 1202, and operates and manages the datacenter (cloud server) 1203. The service provider 1120 provides the service using the OS 1202 and the application 1201 managed by the datacenter operation company 1110.

In all of the types of the cloud services explained above, the service provider 1120 provides the services. For example, the service provider or the datacenter operation company may develop an OS, an application, a database of big data, and the like by itself or may cause an outsider to develop the OS, the application, the database of big data, and the like.

Note that, irrespective of the types of the cloud services, the apparatus 1101 (e.g., a smartphone or a PC) alone shown in FIG. 1 may configure the interactive system 10. For example, the knowledge base 206 may be disposed on a network on the outside of the apparatus 1101 to configure the interactive system 10 from the knowledge base 206 and the apparatus 1101.

Forms realized by optionally combining the components and the functions explained in the embodiment are also included in the scope of the present disclosure.

The present disclosure can be used as an interactive system that provides information through interaction such as a medical interview.

What is claimed is:

1. An information processing method in an interactive apparatus that questions a symptom of a user through interaction with the user, the interactive apparatus including:
   a frontend configured to exchange information expressed in a natural language with a user;

a knowledge base including a storage medium storing information including symptoms and diseases associated with each other;

a backend configured to perform processing including provision of information based on search processing to the knowledge base; and an agent configured to perform an exchange of a dialogue act with respective one of the frontend and the backend, wherein the frontend, the agent and the backend include a computer, the information processing method comprising:

causing the computer of the frontend to:

output first question information of a first type concerning the symptom of the user to a display connected to the interactive apparatus or a speaker connected to the interactive apparatus, the first question information indicating an open question;

receive first answer information in the natural language indicating an answer to the question indicated by the first question information from a keyboard connected to the interactive apparatus, a touch panel connected to the interactive apparatus, or a microphone connected to the interactive apparatus;

convert, using a natural language understanding technique, the first answer information in the natural language into a dialogue act, which is a combination of a symptom included in the first answer information and a dialogue act type, the dialogue act type being one of a plurality of predetermined values; and add, using the natural language understanding technique, reliability of a result of the natural language understanding technique to the dialogue act, causing the computer of the agent to:

obtain, from the computer of the front end, the dialogue act with the reliability of the result of the natural language understanding technique;

separate the dialogue act into the dialogue act type and the symptom;

determine the dialogue act type to be output based on a series of dialogue act types in the past, without performing determination based on the symptom in the dialogue act according to magnitude comparison between the obtained reliability of the result of the natural language understanding technique and a threshold of reliability set in advance, wherein the dialogue act type is determined without confirming with the frontend before the dialogue act obtained from the frontend is output to the backend when the reliability of the result of natural language understanding technique obtained with the dialogue act from the computer of the frontend is higher than the threshold of the reliability set in advance, and the dialogue act is confirmed with the frontend when the reliability of the result of natural language understanding technique obtained with the dialogue act from the computer of the frontend is lower than the threshold of the reliability set in advance;

output second question information of the first type concerning the symptom of the user to the display or the speaker based on the dialogue act type to be output determined by the agent, in a case where the computer of the agent determines that the answer indicated by the first answer information does not include a negative word, the second question information indicating an open question; and output third question information of a second type concerning the symptom of the user to the display or the speaker based on the dialogue act type to be output determined by the agent, in a case where the computer of the agent determines that the answer indicated by the first answer information includes the negative word, the third question information indicating a closed question;

causing the computer of the frontend to receive second answer information from the keyboard, the touch panel or the microphone, the second answer information indicating presence or absence of the symptom indicated by the third question information of the second type;

causing the computer of the agent to:

determine presence or absence of the symptom indicated by the third question information based on the second answer information;

in a case where the computer of the agent determines that the symptom indicated by the third question information is present, classify the symptom indicated by the third question information as a designated keyword; and in a case where the computer of the agent determines that the symptom indicated by the third question information is absent, classify the symptom indicated by the third question information as an excluded keyword;

causing the computer of the backend to perform a search of the knowledge base based on a combination of the designated keyword and the excluded keyword;

causing the computer of the agent to acquire a conclusion from the backend, the conclusion including at least one disease; and causing the computer of the frontend to output information to the display or the speaker, the information indicating a disease of the user identified based on a combination of the designated keyword and the excluded keyword being provided from the agent to the frontend.

2. The information processing method according to claim 1, wherein the open question is a question other than a question to be answered by yes or no, and the closed question is a question to be answered by yes or no.

3. The information processing method according to claim 1, wherein the computer of the agent repeats outputting the third question information until a number of results of the search by the backend is equal to or smaller than a predetermined number.

4. The information processing method according to claim 1, wherein the computer of the backend performs the search of the knowledge base for a disease that is associated with the symptom classified as the designated keyword, and is not associated with the symptom classified as the excluded keyword in the knowledge base.

5. The information processing method according to claim 1, wherein the first answer information in the natural language is converted into the dialogue act including a first dialogue act type when the answer indicated by the first answer information does not include the negative word, and the first answer information in the natural language is converted into the dialogue act including a second dialogue act type when the answer indicated by the first answer information includes the negative word, the second dialogue act type is different from the first dialogue act type.

6. A non-transitory recording medium having recorded therein a computer program causing a processor to execute information processing in an interactive apparatus that questions a symptom of a user through interaction with the user, the interactive apparatus including:
  a frontend configured to exchange information expressed in a natural language with a user;
  a knowledge base including a storage medium storing information including symptoms and diseases associated with each other;
  a backend configured to perform processing including provision of information based on search processing to the knowledge base; and
  an agent configured to perform an exchange of a dialogue act with respective one of the frontend and the backend, wherein the frontend, the agent and the backend include the processor,
  the information processing comprising:
  causing the computer of the frontend to:
    output first question information of a first type concerning the symptom of the user to a display connected to the interactive apparatus or a speaker connected to the interactive apparatus, the first question information indicating an open question;
    receive by the frontend, first answer information in the natural language indicating an answer to the question indicated by the first question information from a keyboard connected to the interactive apparatus, a touch panel connected to the interactive apparatus, or a microphone connected to the interactive apparatus;
    convert, using a natural language understanding technique, the first answer information in the natural language into a dialogue act, which is a combination of a symptom included in the first answer information and a dialogue act type, the dialogue act type being one of a plurality of predetermined values; and
    add, using the natural language understanding technique, reliability of a result of the natural language understanding technique to the dialogue act,
  causing the computer of the agent to:
    obtain, from the computer of the front end, the dialogue act with the reliability of the result of the natural language understanding technique;
    separate the dialogue act into the dialogue act type and the symptom;
    determine the dialogue act type to be output based on a series of dialogue act types in the past, without performing determination based on the symptom in the dialogue act according to magnitude comparison between the obtained reliability of the result of the natural language understanding technique and a threshold of reliability set in advance,
    wherein the dialogue act type is determined without confirming with the frontend before the dialogue act obtained from the frontend is output to the backend when the reliability of the result of natural language understanding technique obtained with the dialogue act from the computer of the frontend is higher than the threshold of the reliability set in advance, and
    the dialogue act is confirmed with the frontend when the reliability of the result of natural language understanding technique obtained with the dialogue act from the computer of the frontend is lower than the threshold of the reliability set in advance;
    output second question information of the first type concerning the symptom of the user to the display or the speaker based on the dialogue act type to be output determined by the agent, in a case where the computer of the agent determines that the answer indicated by the first answer information does not include a negative word, the second question information indicating an open question; and
    output third question information of a second type concerning the symptom of the user to the display or the speaker based on the dialogue act type to be output determined by the agent, in a case where the computer of the agent determines that the answer indicated by the first answer information includes the negative word, the third question information indicating a closed question;
  causing the computer of the frontend to receive second answer information from the keyboard, the touch panel or the microphone, the second answer information indicating presence or absence of the symptom indicated by the third question information of the second type;
  causing the computer of the agent to:
  determine presence or absence of the symptom indicated by the third question information based on the second answer information;
  in a case where the computer of the agent determines that the symptom indicated by the third question information is present, classify the symptom indicated by the third question information as a designated keyword;
  in a case where the computer of the agent determines that the symptom indicated by the third question information is absent, classify the symptom indicated by the third question information as an excluded keyword;
  causing the computer of the backend to perform a search of the knowledge base based on a combination of the designated keyword and the excluded keyword;
  causing the computer of the agent to acquire a conclusion from the backend, the conclusion including at least one disease; and
  causing the computer of the frontend to output information to the display or the speaker, the information indicating a disease of the user identified based on a combination of the designated keyword and the excluded keyword being provided from the agent to the frontend.

7. An information processing method in an interactive apparatus that interacts with a user to narrow down items to an item that the user desires to find, the interactive apparatus including:
  a frontend configured to exchange information expressed in a natural language with a user;
  a knowledge base including a storage medium storing information including items and keywords associated with each other;
  a backend configured to perform processing including provision of information based on search processing to the knowledge base; and
  an agent configured to perform an exchange of a dialogue act with respective one of the frontend and the backend, wherein the frontend, the agent and the backend include a computer,
  the information processing method comprising:
  causing the computer of the frontend to:
    output first question information of a first type concerning the item that the user desires to find to a display connected to the interactive apparatus or a speaker connected to the interactive apparatus, the first question information indicating an open question;

receive first answer information in the natural language indicating an answer to the question indicated by the first question information from a keyboard connected to the interactive apparatus, a touch panel connected to the interactive apparatus, or a microphone connected to the interactive apparatus;

convert, using a natural language understanding technique, the first answer information in the natural language into a dialogue act, which is a combination of incidental information included in the first answer information and a dialog act type, the dialogue act type being one of a plurality of predetermined values; and add, using the natural language understanding technique, reliability of a result of the natural language understanding technique to the dialogue act, causing the computer of the agent to:

obtain, from the computer of the front end, the dialogue act with the reliability of the result of the natural language understanding technique;

separate the dialogue act into the dialogue act type and the incidental information;

determine by the agent, the dialogue act type to be output based on a series of dialogue act types in the past, without performing determination based on the incidental information in the dialogue act according to magnitude comparison between the obtained reliability of the result of the natural language understanding technique and a threshold of reliability set in advance, wherein the dialogue act type is determined without confirming with the frontend before the dialogue act obtained from the frontend is output to the backend when the reliability of the result of natural language understanding technique obtained with the dialogue act from the computer of the frontend is higher than the threshold of the reliability set in advance, and the dialogue act is confirmed with the frontend when the reliability of the result of natural language understanding technique obtained with the dialogue act from the computer of the frontend is lower than the threshold of the reliability set in advance;

output second question information of the first type concerning the item that the user desires to find to the display or the speaker based on the dialogue act type to be output determined by the agent, in a case where the computer of the agent determines that the answer indicated by the first answer information does not include a negative word, the second question information indicating an open question;

output third question information of a second type concerning the item that the user desires to find to the display or the speaker based on the dialogue act type to be output determined by the agent, in a case where the computer of the agent determines that the answer indicated by the first answer information includes the negative word, the third question information indicating a closed question;

causing the computer of the frontend to receive second answer information from the keyboard, the touch panel or the microphone, the second answer information indicating whether an item indicated by the third question information relates to the item that the user desires to find;

causing the computer of the agent to:

determine whether the item indicated by the third question information relates to the item that the user desires to find based on the second answer information;

in a case where the computer of the agent determines that the item indicated by the third question information relates to the item that the user desires to find, classify the item indicated by the third question information as a designated keyword;

in a case where the computer of the agent determines that the item indicated by the third question information does not relate to the item that the user desires to find, classify the item indicated by the third question information as an excluded keyword;

causing the computer of the backend to perform a search of the knowledge base based on a combination of the designated keyword and the excluded keyword;

causing the computer of the agent to acquire a conclusion from the backend, the conclusion including at least one item stored in the knowledge base; and causing the computer of the frontend to output information to the display or the speaker, the information indicating an item that the user desires to find identified based on a combination of the designated keyword and the excluded keyword being provided from the agent to the frontend.

8. The information processing method according to claim 7, wherein the item that the user desires to find is any of a disease name, a recipe of a dish, a travel plan, a real estate property, and a video content.

9. The information processing method according to claim 7, wherein the open question is a question other than a question to be answered by yes or no, and the closed question is a question to be answered by yes or no.

10. A non-transitory recording medium having recorded therein a computer program causing a processor to execute information processing in an interactive apparatus that interacts with a user to narrow down items to an item that the user desires to find, the interactive apparatus including:

a frontend configured to exchange information expressed in a natural language with a user;

a knowledge base including a storage medium storing information including items and keywords associated with each other;

a backend configured to perform processing including provision of information based on search processing to the knowledge base; and an agent configured to perform an exchange of a dialogue act with respective one of the frontend and the backend, wherein the frontend, the agent and the backend include the processor, the information processing method comprising:

causing the computer of the frontend to:

output first question information of a first type concerning the item that the user desires to find to a display connected to the interactive apparatus or a speaker connected to the interactive apparatus, the first question information indicating an open question;

receive first answer information in the natural language indicating an answer to the question indicated by the first question information from a keyboard connected to the interactive apparatus, a touch panel connected to the interactive apparatus, or a microphone connected to the interactive apparatus;

convert, using a natural language understanding technique, the first answer information in the natural language into a dialogue act, which is a combination of incidental information included in the first answer information and a dialog act type, the dialogue act type being one of a plurality of predetermined values; and add, using the natural language understanding technique, reliability of a result of the natural language understanding technique to the dialogue act, causing the computer of the agent to:

obtain, from the computer of the front end, the dialogue act with the reliability of the result of the natural language understanding technique;

separate the dialogue act into the dialogue act type and the incidental information;

determine the dialogue act type to be output based on a series of dialogue act types in the past, without performing determination based on the incidental information in the dialogue act according to magnitude comparison between the obtained reliability of the result of the natural language understanding technique and a threshold of the reliability set in advance, wherein the dialogue act type is determined without confirming with the frontend before the dialogue act obtained from the frontend is output to the backend when the reliability of the result of natural language understanding technique obtained with the dialogue act from the computer of the frontend is higher than the threshold of the reliability set in advance, and the dialogue act is confirmed with the frontend when the reliability of the result of natural language understanding technique obtained with the dialogue act from the computer of the frontend is lower than the threshold of the reliability set in advance;

output second question information of the first type concerning the item that the user desires to find to the display or the speaker based on the dialogue act type to be output determined by the agent, in a case where the computer of the agent determines that the answer indicated by the first answer information does not include a negative word, the second question information indicating an open question;

output third question information of a second type concerning the item that the user desires to find to the display or the speaker based on the dialogue act type to be output determined by the agent, in a case where the computer of the agent determines that the answer indicated by the first answer information includes the negative word, the third question information indicating a closed question;

causing the computer of the frontend to receive second answer information from the keyboard, the touch panel or the microphone, the second answer information indicating whether an item indicated by the third question information relates to the item that the user desires to find;

causing the computer of the agent to:

determine whether the item indicated by the third question information relates to the item that the user desires to find based on the second answer information;

in a case where the computer of the agent determines that the item indicated by the third question information relates to the item that the user desires to find, classify the item indicated by the third question information as a designated keyword;

in a case where the computer of the agent determines that the item indicated by the third question information does not relate to the item that the user desires to find, classify the item indicated by the third question information as an excluded keyword;

causing the computer of the backend to perform a search of the knowledge base based on a combination of the designated keyword and the excluded keyword;

causing the computer of the agent to acquire a conclusion from the backend, the conclusion including at least one item stored in the knowledge base; and causing the computer of the frontend to output information to the display or the speaker, the information indicating an item that the user desires to find identified based on a combination of the designated keyword and the excluded keyword being provided from the agent to the frontend.

\* \* \* \* \*